United States Patent [19]

Bramlet

[11] Patent Number: 5,649,946

[45] Date of Patent: Jul. 22, 1997

[54] CARPAL TUNNEL MEDICAL INSTRUMENT

[76] Inventor: Dale G. Bramlet, 2044 Brightwaters Blvd. NE., St. Petersburg, Fla. 33704-3010

[21] Appl. No.: 406,556

[22] Filed: Mar. 20, 1995

[51] Int. Cl.⁶ .................................................. A61B 17/32
[52] U.S. Cl. ......................... 606/167; 606/170; 606/159
[58] Field of Search .............................. 604/167, 168, 604/170, 159, 160, 162, 96, 22, 164

[56] References Cited

U.S. PATENT DOCUMENTS

| | | | |
|---|---|---|---|
| 4,962,770 | 10/1990 | Agee et al. | 606/170 |
| 4,997,419 | 3/1991 | Lakatos et al. | 606/190 |
| 5,323,765 | 6/1994 | Brown | 606/170 |
| 5,413,580 | 5/1995 | Stephenson | 606/167 |

*Primary Examiner*—Michael Buiz
*Assistant Examiner*—Kevin Truong
*Attorney, Agent, or Firm*—Rudnick & Wolfe

[57] ABSTRACT

A carpal tunnel medical instrument that facilitates a two-handed carpal tunnel surgical procedure. The medical instrument of the present invention includes an elongated handle with a surgical instrument extending from one end thereof at an acute angle of about 90 degrees but in substantially the same plane as the handle. The surgical instrument is configured as either a dual channelled cannula, a cutting blade, a rasp, a probe or nerve hook.

38 Claims, 23 Drawing Sheets

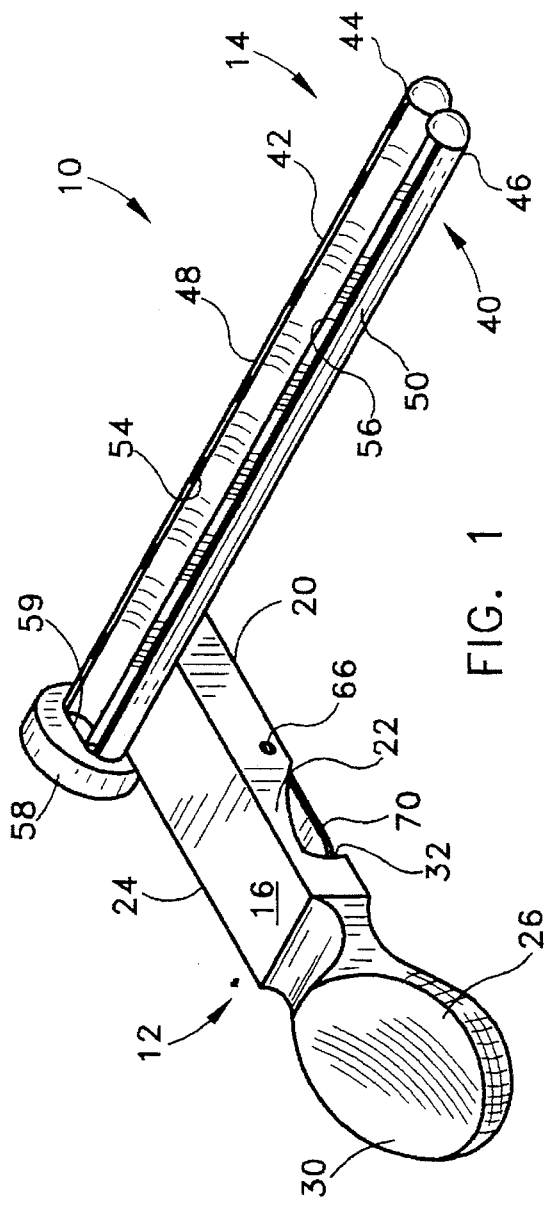
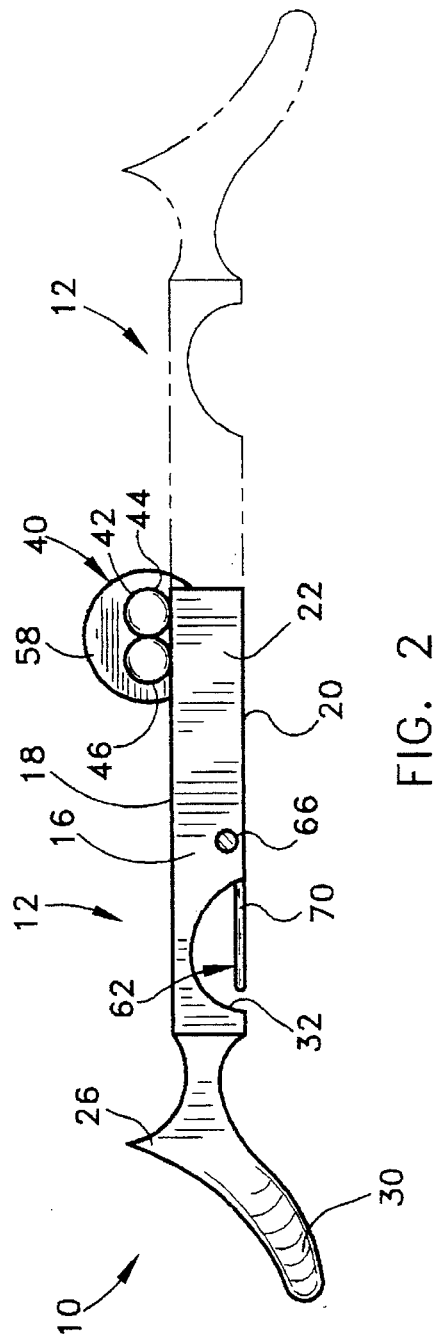
FIG. 1
FIG. 2

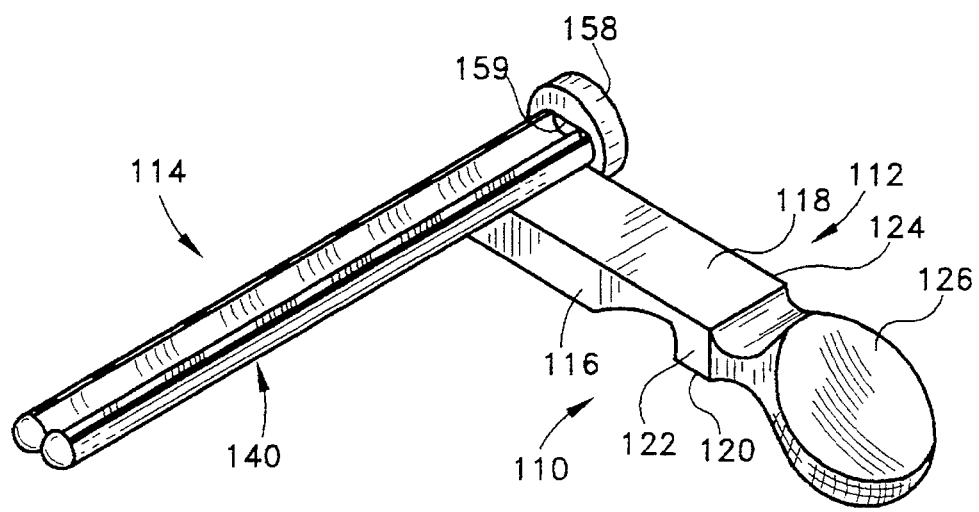
FIG. 14
FIG. 15
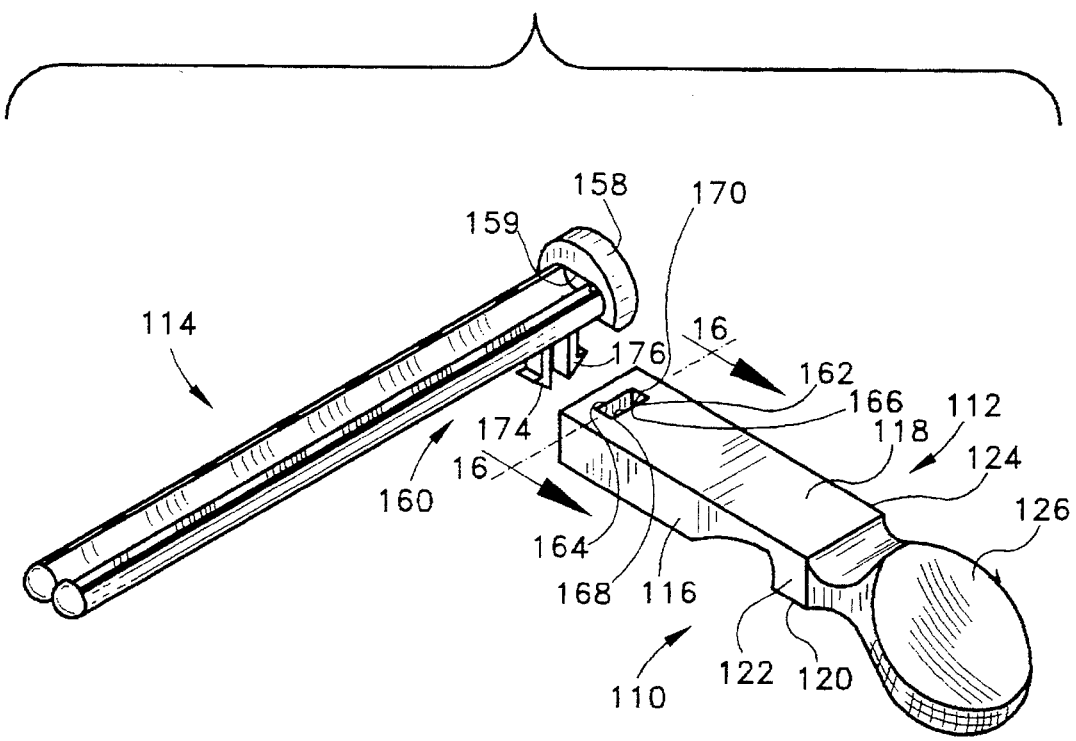

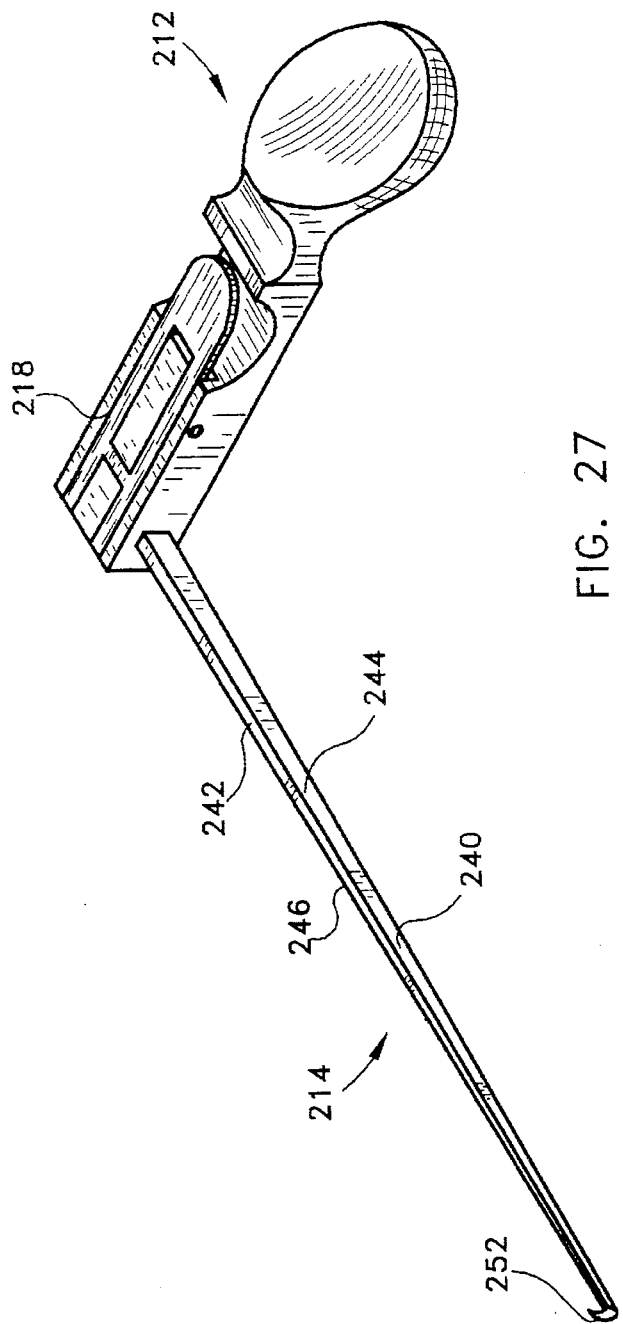
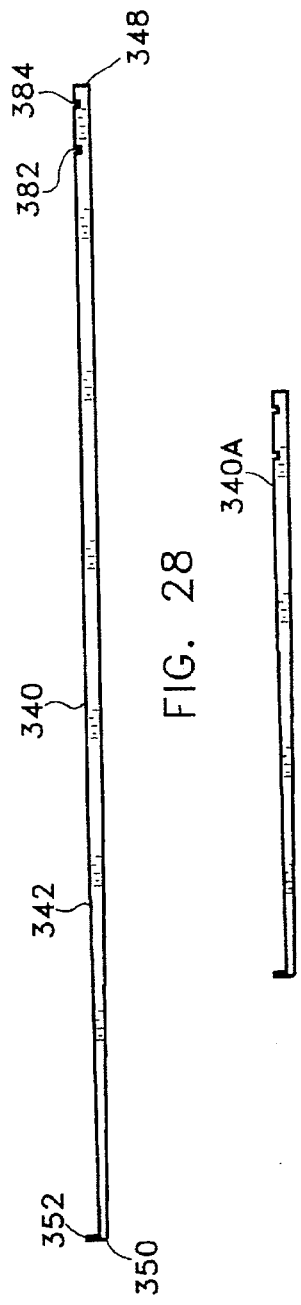
FIG. 27
FIG. 28
FIG. 29

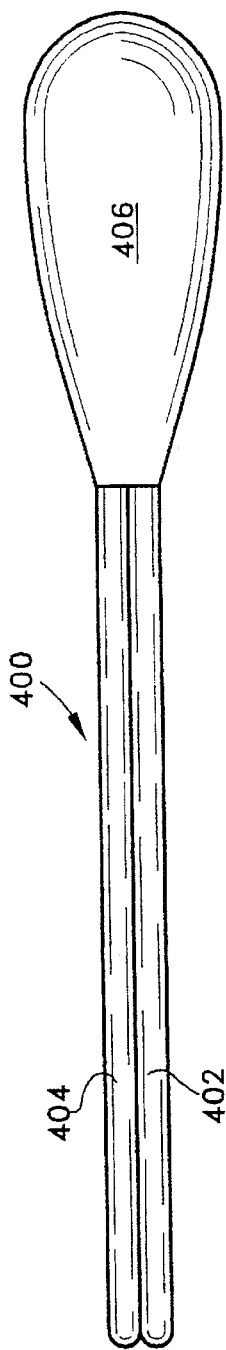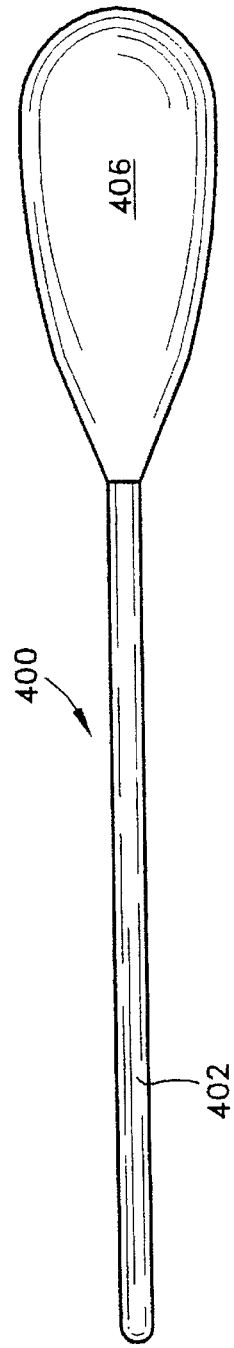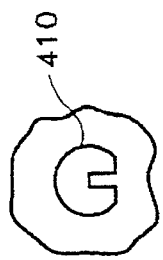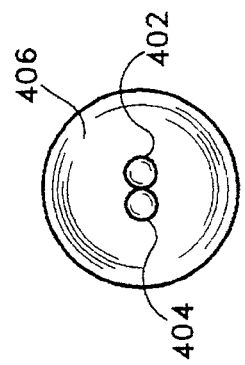

CARPAL TUNNEL MEDICAL INSTRUMENT

FIELD OF THE INVENTION

The present invention generally relates to medical instruments and, more particularly, to a carpal tunnel medical instrument having a surgical instrument extending at about a 90 degree angle relative to a handle.

BACKGROUND OF THE INVENTION

In the late 1980s, a new surgical procedure was introduced into the United States to relieve discomfort in those patients with documented signs and symptoms of a condition which has since become known as carpal tunnel syndrome. Carpal tunnel syndrome results from the compression of a person's median nerve. The surgical procedure to relieve carpal tunnel syndrome involves the release of the transverse carpal ligament. Carpal tunnel syndrome is a condition widely occurring in the United States and has become one of the major health and industrial medicine concerns of the 20th century. The loss of wages and time off work have approached hundreds of millions of dollars just in the United States.

As will be appreciated, techniques and devices that can lead to a patient's early return to work, lowered morbidity, and early return of grip strength can have an enormous cost savings for employers, and have significantly gained in popularity in the last few years. One of the main advantages of carpal tunnel release surgery is the ability to perform bilateral medical procedures without the concomitant need for splinting or casting of both arms of the patient, which can lower the total cost of medical care of patients with bilateral carpal tunnel syndrome, representing about 80% of patients with this condition. The cost savings can approach about 40% to about 60% by effecting bilateral carpal tunnel release surgeries, notwithstanding the enormous savings to employers realized by the patient's reduced time away from work and the employers saved benefits concerning workman's compensation.

An essential technique used during carpal tunnel release surgery is one involving arthroscopy. The technique of arthroscopy was initially developed and used for knee surgery procedures in the 1920s. The basic technique for knee arthroscopy has since been applied to shoulder, ankle, wrist, and virtually every other joint in the body. Arthroscopy is generally regarded as a "two-handed" technique.

Dr. James C. Y. Chow has developed a two-portal surgical technique for effecting the release of the transverse carpal ligament. Avoiding human structures such as the superficial palmar arch, the common digital nerve to the third web space, and avoiding the ulnar bursa are requisite to successful release of the transverse carpal ligament. The "Chow technique" facilitates the displacement, to a slight degree, and from the operative field of view, of the ulnar bursa and other human structures that the surgeon would not wish to cut during the carpal tunnel release surgical procedure. Removal of such human structures allows the surgeon to obtain a clearer visual field thus reducing the risk to such human structures when the carpal ligament is released.

A main disadvantage of the "Chow technique" is that this two portal technique involves the risk to adjacent neurovascular structures. Another drawback of the "Chow technique" involves the significant morbidity that a doctor is trying to avoid of a painful palmar incision. Furthermore, the "Chow technique" fails to allow both the displacement from the operative field of those structures the surgeon wishes to avoid cutting simultaneously with the use of surgical instruments for cutting and, thus, effecting the release of the transverse carpal ligament. Accordingly, one medical instrument is inserted to displace the human structures that are not to be cut. After removing the human structures from the operative field of view, that medical instrument is withdrawn and another medical instrument is inserted to cut the ligament. This procedure is repeated as needed during the surgery. Once the retracting medical instrument, commonly known as a probe, is removed from the cannula and prior to the surgical cutting instrument, commonly known as a blade, is replaced into the cannula, the human structures that should not be cut may redisplace back into the operative field of view, thus requiring the surgeon to again insert the probe in an attempt to again remove the human structures from the operative field of view.

Dr. John M. Agee has proposed an endoscopic carpal ligament release surgical approach that attempts to avoid the painful palmar incision inherent with the "Chow technique". The "Agee technique" proposes a single surgical incision in the less painful proximal incision site just proximal to the wrist flexion crease. Dr. Aree further proposes a single hand held device that couples a blade assembly, used to surgically cut the carpal ligament, with an endoscope. Thus, the "Agee technique" advantageously enables a single operator to perform the carpal tunnel release.

Like the "Chow technique", however, one major drawback with the "Agee technique" is the inability of the surgeon to use surgical instruments in both hands. That is, the "Agee technique" does not teach or disclose allowing the surgeon to use both hands during carpal tunnel release surgery in order to push or pull any human structures that may obfuscate or be within the operative field of view while simultaneously using surgical instruments to cut or sever the transverse carpal ligament.

Known carpal tunnel release surgical procedures and those carpal tunnel release devices on the market do not allow the flexibility inherent with traditional arthroscopic surgery to be used to its fullest potential. Known carpal tunnel release surgical procedures and those carpal tunnel release surgical devices that are publicly available do not lend themselves or permit a two-handed surgical technique to be used during carpal tunnel release surgery. That is, no known technique or known device allows a surgeon to use one hand to manipulate one surgical instrument to remove human structures that are not intended to be cut during the procedure from the operative field of view while simultaneously allowing the surgeon to use the other hand to manipulate a second surgical instrument to effectively cut the transverse carpal ligament.

As will be appreciated by those skilled in the art, the carpal canal into which the endoscope is introduced is limited by its transverse cross-sectional area through which pass nine flexor tendons and the median nerve. Thus, the area in which the carpal tunnel release surgery is to be effected is replete with human structures in addition to the transverse carpal ligament that is to be cut during the carpal tunnel release surgical procedure. The most common complications arising from carpal tunnel release surgery involving use of an endoscope concern the risks to the common digital nerve to the third web space being either lacerated, contused or injured, either at the proximal or distal portal with passage of the endoscope.

The Agee device uses a flat-topped surface to enable the operator to push human structures out of the operative field of view of the endoscope. The "Agee technique" and known devices used in combination therewith, however, is not and does not involve a two-handed technique, as traditionally employed in arthroscopy. That is, and while offering an advancement over other techniques, the Agee device does not allow the surgeon to use one hand to manipulate and move human structure other than that to be cut from the operative field of view while allowing the surgeon to use the other hand to cut the transverse carpal tunnel ligament of the carpal canal.

Smith+Nephew Dyonics of Andover, Mass. offers a carpal ligament release system that utilizes two portals, a distinct theoretical disadvantage from a patient's perspective. In the Dyonics system, stability of a surgical cannula is obtained by both a proximal and distal incision. As will be appreciated, any successful carpal tunnel release system must be reasonably stable and yet have flexibility in the depth of cut. The Dyonics System, however, allows only a single operative hand to be used to manipulate an instrument for release of the transverse carpal ligament. The operating surgeon frequently is taught to utilize either a q-tip or nerve hook to try to tease unwanted structures from the operative field, but the simultaneous retraction of the structure while one is cutting is not possible with the Dyonics system. Moreover, the technique of holding the cutting blade in the Dyonics System requires the surgeon to hold the cutting blades in a palm-down, pronated position. This is not a natural surgical technique and must be taught. Allowing the surgeon to hold the knives like one would hold a pencil is a more traditional approach to surgery and one that surgeons are readily familiar with.

As will be appreciated, allowing a surgeon to use both hands during carpal tunnel release surgery while still allowing a traditional approach to surgery would normally appear to have significant drawbacks. That is, since some surgeons are left hand dominant while other surgeons are right hand dominant, some of the carpal tunnel medical instruments must be specifically designed for the right hand dominant surgeons while other carpal tunnel medical instruments must be specifically designed for the left hand dominant surgeons. Thus, and so as to allow a surgeon to feel as comfortable as possible during this relatively delicate surgery, duplicative sets of medical instruments, some configured for right hand dominant surgeons and others configured for left hand dominant surgeons, would appear to be required to perform a two-handed carpal tunnel release surgical technique or approach. Requiring a medical facility, such as a hospital where medical costs are such a serious concern, to carry and inventory duplicate sets or kits of carpal tunnel medical instruments would appear to direct away from the using of a two-handed approach or technique.

Thus, there remains a need and a desire for medical instruments that are flexible enough to allow for two-handed surgical procedures involving the release of the transverse carpal ligament while remaining cost effective.

SUMMARY OF THE INVENTION

In view of the above, and in accordance with the present invention, there is provided a carpal tunnel medical instrument that facilitates a two-handed surgical procedure to release a transverse carpal ligament in a patient. In accordance with one form of the invention, the medical instrument comprises an elongated handle having a surgical instrument releasably connected thereto and extending therefrom at an acute angle of preferably about 90 degrees and in substantially the same plane relative to each other. According to one aspect of the present invention, the handle and surgical instrument comprising the medical instrument are releasably secured to each other. Thus, the medical instrument of the present invention allows the handle to extend from either side of the surgical instrument while maintaining the same orientation between the handle and the surgical instrument thereby enhancing the versatility of the medical instrument to either left or right hand dominant surgeons.

In a most preferred form of the present invention, the handle and the surgical instrument comprising the carpal tunnel medical instrument are each formed from materials that allow both the handle and the surgical instrument to be sterilized and reused in another carpal tunnel release surgical procedure. In this regard, and according to one aspect of the invention, a locking mechanism releasably secures the surgical instrument to the handle.

It is also within the spirit and scope of the present invention to have a reusable handle releasably attached to a disposable surgical instrument. Thus, after the carpal tunnel release surgery is completed, the surgical instrument is discarded and the handle is sterilized and stored for reuse during another carpal tunnel release surgery. Moreover, it is within the spirit and scope of the present invention that the handle and surgical instrument of the carpal tunnel medical instrument be formed as an integral unit. Where the carpal tunnel medical instrument is a one-piece unit, the handle and surgical instrument are each formed from a material that is suitable for use during the surgery and yet can be cost effectively discarded following the carpal tunnel release surgery.

Regardless of whether the components comprising the medical instrument of the present invention are reusable or discardable, the handle of the medical instrument is preferably configured with a grip at that end of the handle distal from the surgical instrument. The grip on the handle promotes stability of the medical instrument and, more particularly, the surgical instrument during a surgical procedure.

In one form of the invention, the surgical instrument that releasably connects to the handle is configured as a probe or nerve hook. The probe includes an instrumentality at a distal end of and extending upwardly from a top surface of the surgical instrument for displacing structure during the surgical procedure.

In another form of the invention, the surgical instrument that releasably connects to the handle is configured as a cutting blade. The blade includes at least one cutting instrumentality at a distal end of and extending upwardly from a top surface of the surgical instrument for cutting or severing the transverse carpal ligament.

In still another alternative form of the invention, the surgical instrument that releasably connects to the handle is configured as a double channelled cannula. The cannula is configured with dual channels, with each channel being configured to accommodate about a 2.3 mm endoscope for endwise movement. Also, each channel in the double cannula opens to the top surface of the surgical instrument.

The double channelled cannula advantageously allows for the simultaneous visualization of the transverse carpal ligament coupled with the use of one or more surgical instruments in the second channel of the cannula. As will be appreciated, the introduction of an arthroscope through one channel of the double channeled cannula provides the surgeon with visualization during the surgical procedure. The adjacent channel of the cannula allows introduction of a first surgical instrument such as a probe for retracting questionable human structures out of the field of view along with simultaneous use of an alternative surgical instrument such as a blade for cutting of the transverse carpal ligament. In this embodiment, each channel of the double channelled cannula is closed at the distal end of the surgical instrument.

In that embodiment of the present invention involving a one-piece or unitary carpal tunnel medical instrument the elongated surgical instrument portion of the instrument is configured as either a probe, nerve hook, cutting blade or a double cannula. Notably, the handle portion of the one-piece instrument extends at an acute angle of about 90° from the surgical instrument portion and in a plane substantially parallel to a planar top surface of the surgical instrument portion. The acute angular formation between the handle portion and the surgical instrument portion thus allowing the surgeon to hold the medical instrument in a traditional approach.

In those embodiments of the medical instruments wherein the surgical instrument is releasably secured to the handle to define an included acute angle of about 90° therebetween, one of the major advantages afforded by the present invention relates to the versatility of the medical instrument. It is important to note, that in addition to having the capability of securing the handle to either side of the surgical instrument, the orientation between the top surface of the surgical instrument and the handle remains consistent. Thus, in those embodiments of the present invention having the handle and surgical instrument releasably secured to each other, the handle and surgical instrument can be coupled in a manner customizing the medical instrument for use with left or right handed dominant surgeons and to promote bilateral surgery.

Because the medical instrument of the present invention can be readily altered to conform to the surgeon, the medical instrument according to the present invention promotes the use of a two-handed technique to perform a carpal tunnel release surgical procedure. This offers the unique advantage for the surgeon to be able to retract offending human structure, such as the common digital nerve or the ulnar bursa, out of the operative field of view with one hand while allowing the surgeon to use the other hand for simultaneous cutting and release of the carpal tunnel ligament without having to remove, replace or alternate surgical instruments. Moreover, configuring the handle at an acute angle of about 90 degrees relative to the surgical instrument, allows the medical instrument of the present invention to be held in a more normal fashion, like a scalpel or a pencil rather than with a pronated, palm down fashion.

The medical instrument that is configured as a double channelled cannula, allows a conventional 2.3 mm endoscope or, preferably, a modified 2.3 mm or smaller endoscope to be introduced through one channel of the cannula. The modified endoscope has a light source coming off at about a 90 degree angle to the 30 degree up-looking scope. As opposed to known systems, the light source or camera end of the modified endoscope can be swivelled such that they are removed from the surgeon's operating field. The bi-channelled cannula thus facilitates simultaneous visualization of the transverse carpal ligament, while another channel in the cannula allows the use of both surgical instruments for retracting questionable human structures from the operative field of view and simultaneous use of another surgical instrument for cutting of the transverse carpal ligament.

These and other features of the present invention will become readily apparent from the following detailed description, appended claims, and formal drawings:

DETAILED DESCRIPTION OF THE FORMAL DRAWINGS

FIG. 1 is a perspective view of one form of medical instrument according to the present invention;

FIG. 2 is a front elevational view of the medical instrument illustrated in FIG. 1, with a phantom line showing of a handle of the instrument in an alternative position;

FIG. 14 is a perspective view of another embodiment of the present invention;

FIG. 15 is a perspective view similar to FIG. 14 showing the component parts of the medical instrument in disassembled relation relative to each other;

FIG. 27 is a perspective view of the medical instrument similar to FIG. 19 showing a handle of the medical instrument releasably secured in an alternative arrangement relative to a surgical instrument;

FIGS. 28 and 29 are schematic side elevational views of alternative forms of surgical instruments, such as probes, that can be used in combination with the medical instrument schematically illustrated in FIGS. 19 through 27;

FIG. 38 is a plan view of one form of obturator that is used in combination with the medical instrument according to the present invention;

FIG. 39 is a side elevational view of the obturator schematically illustrated in FIG. 38;

FIG. 40 is a front elevational view of the obturator schematically illustrated in FIG. 38;

FIG. 41 is an enlarged front elevational view of an obturator that is configured for use with the alternative dual channeled cannula schematically illustrated in FIGS. 11 and 13;

DETAILED DESCRIPTION OF THE PRESENT INVENTION

Figure 5:
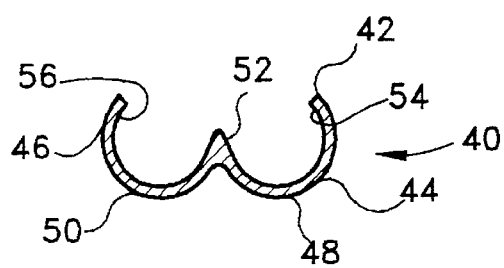
FIG. 5 is a sectional view taken along line 5—5 of FIG. 3.

While the present invention is susceptable of embodiment in various forms, there are shown in the drawings and will hereinafter be described, preferred embodiments of the invention with the understanding that the present disclosure is to be considered as setting forth exemplifications of the invention and that such exemplifications are not intended to limit the invention to the specific embodiments illustrated.

Referring now to the drawings, wherein like reference numerals refer to like parts throughout the several views, in FIGS. 1 and 2 there is schematically represented a carpal tunnel medical instrument generally represented in its entirety by reference numerical 10. The medical instrument 10 includes an elongated handle 12 with a surgical instrument 14 arranged in releasable association with the handle 12.

As shown, handle 12 has an elongated configuration that extends generally perpendicular or normal to the longitudinal axis of the surgical instrument 14. Handle 12 includes a body 16 having a top surface 18, a bottom surface 20, a front face 22, and a rear face 24. Body 16 preferably further defines a grip portion 26 at that end of the body 16 opposite from which the surgical instrument 14 releasably attaches. As shown, grip portion 26 is ergonomically configured to facilitate a key pinch hold on the medical instrument 10 thus rendering it stable.

As shown in FIG. 2, the grip portion 26 of the handle 12 is preferably configured with a finger 30 that is preferably arcuate and slants downwardly and away from the top and bottom surfaces 18 and 20, respectively, of the body 16. As shown in FIG. 1, the bottom surface 20 of body 16 is further configured with a concave recess 32 extending between the front and rear faces 22 and 24, respectively, and adjacent or proximate to the finger 30.

Figure 3:
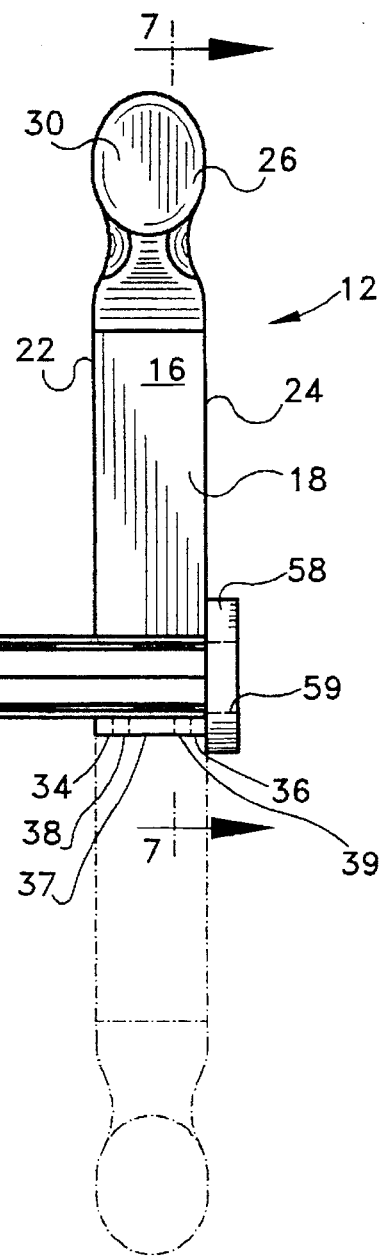
FIG. 3 is a plan view of the medical instrument illustrated in FIG. 1, with a phantom line showing of a handle of the instrument in an alternative position.
Figure 4:
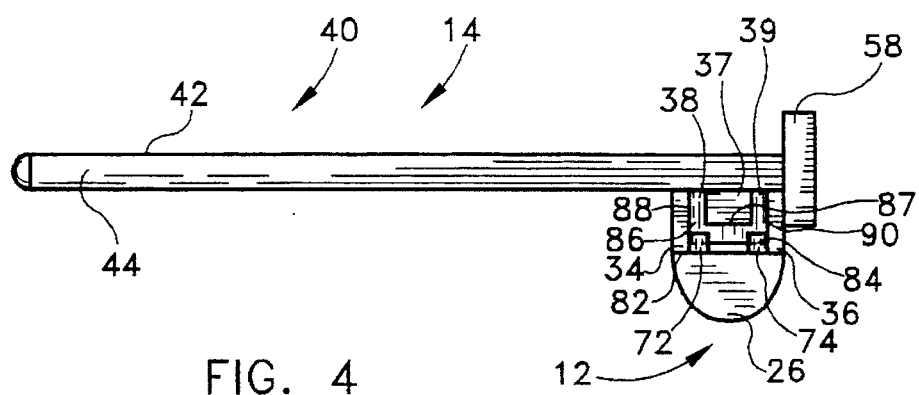
FIG. 4 is a side view of the medical instrument schematically shown in FIG. 3.

At that end opposite from finger 30, and as shown in FIGS. 3 and 4, the body 16 of handle 12 is configured with a pair of fore-and-aft spaced and generally parallel arms 34 and 36. Body 16 further defines a line 37 that extends parallel to and between the arms 34 and 36. As shown, line 37 is substantially coextensive with arms 34 and 36. Body 16 further defines a pair of channels or openings 38 and 39 that extend between the tine 37 and arms 34 and 36, respectively. Notably, the channels 38 and 39 open to the top and bottom surfaces 18 and 20, respectively, and to the free end of body 16.

In the embodiment of the invention illustrated in FIGS. 1 through 7, the surgical instrument 14 releasably secured to the handle 12 is a rigid double channelled cannula 40. In the illustrated embodiment, cannula 40 is preferably formed from a suitable rigid material such as stainless steel, titanium or any other suitable material to promote sterilization and reuse of the cannula 40. Alternatively, the cannula 40 could be formed of rigid clear acrylic or clear plastic to enable the surgeon to visualize structures within the carpal canal.

As shown in FIG. 2, the cannula 40 defines a top surface 42 and a pair of generally parallel side surfaces 44 and 46. As shown in FIGS. 1, 3 and 5, the cannula 40 comprises a pair of side-by-side elongated members 48 and 50 having a common elongated center rib or wall 52 that separates a pair of elongated channels 54 and 56 that each open to the top surface 42 of the cannula. Preferably, the channels 54 and 56 are of equal size and approximate 2.8 mm. each in diameter. In effect, the channels 54 and 56 are configured to allow a conventional 2.3 mm. diameter endoscope to be introduced and moved endwise through and along each channel 54 and 56 of the cannula 40. Each channel 54, 56 ranges between about 6 cm. and about 12 cm. in length.

In the embodiment illustrated in FIGS. 3 and 4, an apertured tie 58 is arranged across and attached to one end of the elongated members 48 and 50 of the cannula 40 to promote the surgeon's grasp of the cannula 40. As illustrated in FIGS. 1 and 3, tie 58 preferably defines a transversely elongated slot 59 that opens to both channels 54 and 56 of cannula 40. In the illustrated embodiment of the invention, when the double cannula 40 is releasably secured to the holder handle 12, tie 58 also serves to locate the double cannula 40 endwise relative to the handle 12. At the opposite end, each member 48, 50 of the cannula 40 is provided with a blunt configuration. In the most preferred form of the invention, each elongated member 48, 50 terminates in a semi-spherical shape that closes off each channel 54 and 56 at the distal end of the double cannula 40.

In that embodiment of the invention where handle 12 and the surgical instrument 14 are releasably secured to each other, a manually operated locking mechanism 60 is provided to releasably secure the handle 12 and surgical instrument 14 to each other. In the embodiment illustrated in FIGS. 1 through 9, the locking mechanism 60 includes a locking lever 62 preferably carried by the handle 12 and which cooperates and combines with a locking apparatus 64 provided on the surgical instrument 14 to releasably secure the instrument 14 to the handle 12.

Figure 6:
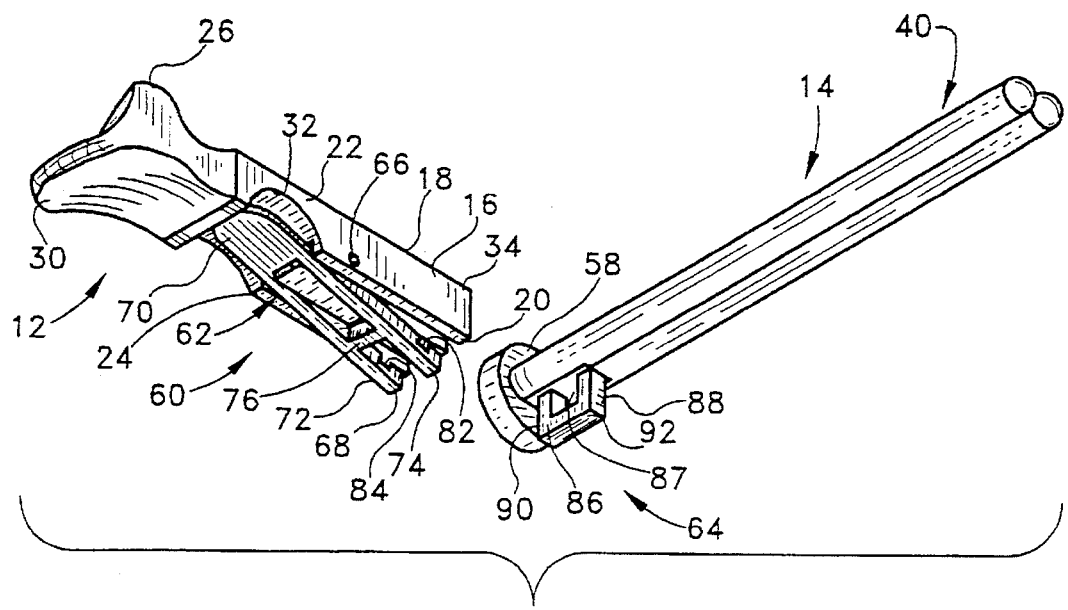
FIG. 6 is a perspective view looking upwardly from an underside of the medical instrument illustrated in FIG. 2.
Figure 7:
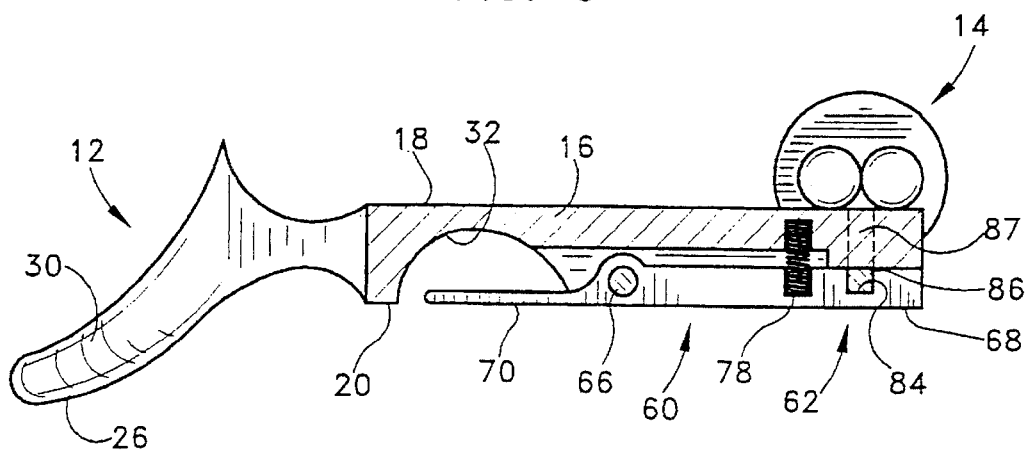
FIG. 7 is a sectional view taken along line 7—7 of FIG. 3, showing one form of locking mechanism used in combination with one embodiment of the invention.
Figure 8:
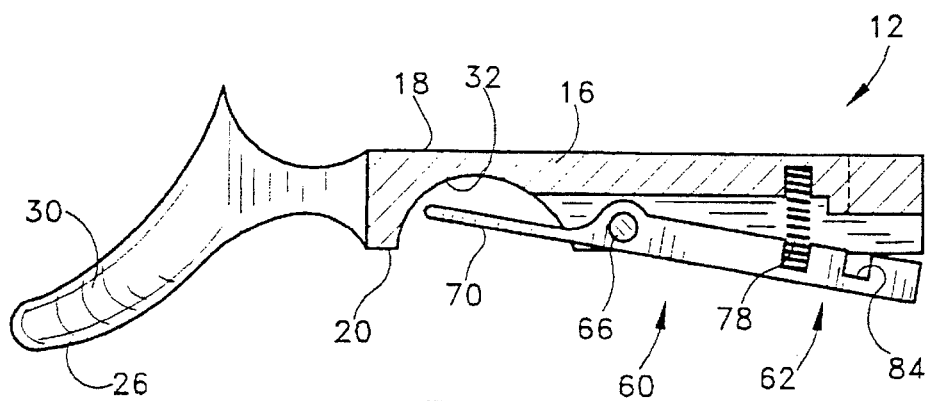
FIG. 8 is a sectional view similar to FIG. 7 but showing the locking mechanism in a released position.

As shown in FIGS. 6 and 7, the locking lever 62 of locking mechanism 60 is mounted toward the underside 20 of the handle 12. More specifically, lever 62 is mounted in a fulcrumed manner to the body 16 of handle 12 preferably by a pivot pin 66 arranged intermediate first and second ends 68 and 70 of the lever 62. As shown in FIG. 7, body 16 is recessed on the underside thereof to accommodate the locking lever 62.

In the illustrated embodiment, locking lever 62 has a generally U-shaped planar configuration including a pair of fore-and-aft spaced generally parallel arms 72 and 74 that extend away from the first end 68 of the lever 62. In a most preferred form of the invention, and as shown in FIG. 6, arms 72 and 74 are rigidly joined to each other intermediate their ends by a brace 76. As shown in FIG. 7, a tension spring 78 is carried between body 16 of handle 12 and lever 62. The purpose of spring 78 is to resiliently bias the locking lever 62 toward a locked or closed position (FIG. 7).

Toward their free ends, the parallel arms 72 and 74 of locking lever 62 define fore-and-aft aligned notches 82 and 84 for purposes to be described hereinafter. At the other or second end 70, the locking lever 62 is designed for manual engagement. As shown in FIGS. 2 and 7, the second end 70 of locking lever 62 terminates in the area of the recess 32 defined in the body 16 of handle 12. As will be appreciated, the recess 32 provides adequate space to allow the free second end 70 of the locking lever 62 to be vertically displaced thus resulting in rocking movement of the locking lever 62 about the axis of pivot pin 66.

Turning to FIGS. 4, 6 and 7, the locking apparatus 64 of locking mechanism 60 cooperates and combines with the locking lever 62 to releasably secure the surgical instrument 14 and the handle 12 to each other. As shown, locking apparatus 64 preferably includes a locking member 86 that is fixedly connected to and depends from the underside of each elongated member 48, 50 of cannula 40. In one form, locking member 86 defines a hole or aperture 87 that corresponds to the cross-sectional configuration of and endwise accommodates the tine 37 on body 16 to prevent vertical displacement of the cannula 40 relative to the body 16 once the surgical instrument 14 is releasably secured to the handle 12. Preferably, locking member 86 further defines a pair of generally parallel and depending surfaces 88 and 90 and an undersurface 92 that extends generally parallel to the top surface 42 of the cannula 40.

Figure 9:
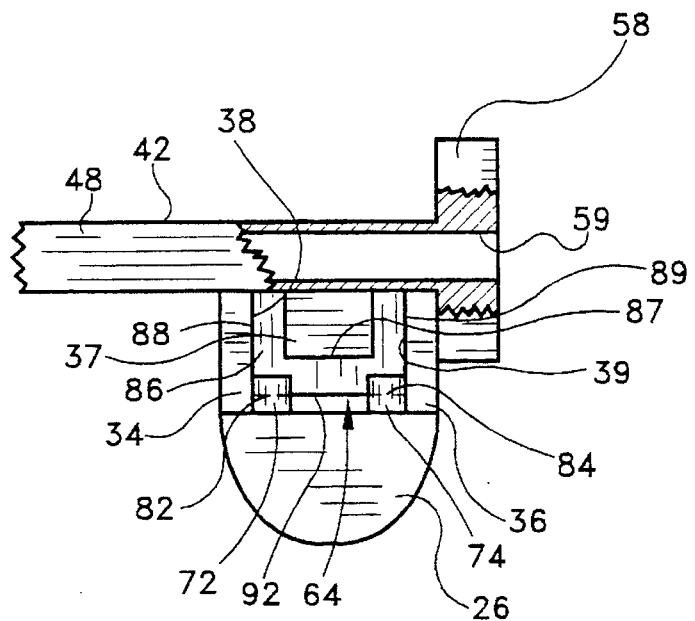
FIG. 9 is a fragmentary enlarged side view of a portion of the present invention.

As shown in FIG. 9, the lock member 86 on the cannula 40 is sized to vertically fit onto the tine 37 defined between arms 34 and 36 on body 16 of handle 12. The depending surfaces 88 and 90 on the depending locking member 86 act in combination with the channels 37 and 39 on the body 16 and serve to guide the locking member 86 into interlocking relationship with tine 37 and furthermore inhibit endwise displacement of the double channelled cannula 40 in either direction along its axis. Once the locking member 86 is positioned over the tine 37 the notches 82, 84 on locking lever 62 positively engage the locking member 86 thus preventing movement of the double channelled cannula 40 relative to the handle 14. The notches 82, 84 on the locking lever 62 and the locking member 86 are configured to fit one within the other when lever 62 is arranged in releasably locked relation relative to the surgical instrument 14.

As will be appreciated, release of the locking mechanism 60 is readily and easily affected by merely pressing upwardly on the second end 70 of the locking lever 62 against the action of spring 78. Application of an upwardly directed force on the second end 70 of the locking lever 62 results in rocking movement of the locking lever 62 about pivot pin 66. Thus, the locking relationship between the notches 82, 84 on locking lever 62 and the locking member 86 of the locking apparatus 64 associated with the double channelled cannula 40 is released. Accordingly, the double channelled cannula 40 can be easily and readily disassembled from the handle 12.

Figure 10:
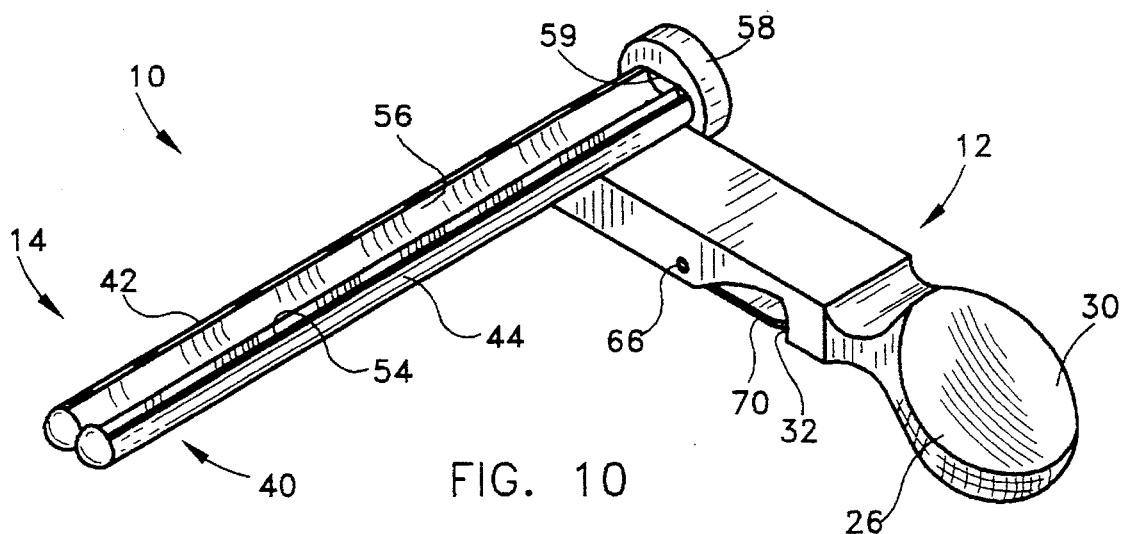
FIG. 10 is a perspective view similar to FIG. 1 but having a handle of the medical instrument releasably secured in an alternative arrangement.

Releasably attaching the handle 12 and surgical instrument 14 to each other allows the handle 12 to be moved to either side of the instrument while maintaining the operative relationship of the double cannula 40 and the handle 12. That is, when the handle is positioned as shown in FIG. 1, handle 12 extends generally perpendicular to and outwardly from the side surface 46 of the double cannula, with the top surface or side 18 of handle 12 in a predetermined relationship relative to the top surface 42 of the cannula 40. Turning now to FIG. 10, when the handle 12 is shifted or moved to a second or alternate position, the handle 12 extends generally perpendicular to and outwardly from the side surface 44 of the cannula 40. It is important to note, however, that although shifted to the opposite side of the cannula 40, the top side or surface 18 of the handle 12 remains in the same predetermined orientation or relation relative to the top surface 42 of the cannula 40.

Figure 11:
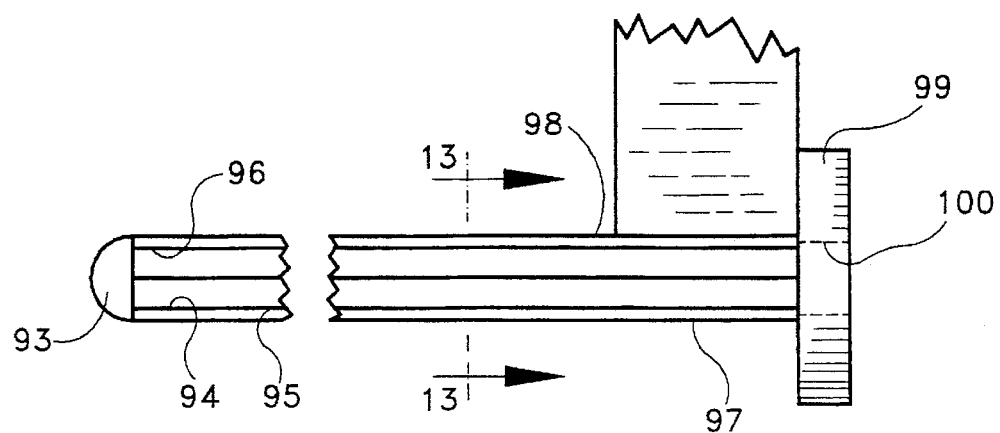
FIG. 11 is an enlarged plan view of an alternative embodiment of a surgical instrument attached to a fragmentary showing of a handle.
Figure 12:
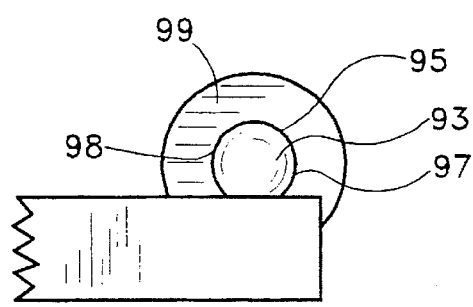
FIG. 12 is an enlarged elevational view of the surgical instrument illustrated in FIG. 11.
Figure 13:
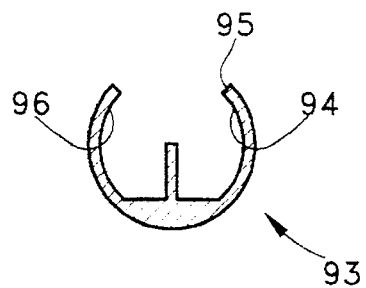
FIG. 13 is a sectional view taken along line 13—13 of FIG. 11.

FIGS. 11, 12 and 13 schematically illustrate an alternative form for the double cannula 40. Rather than structuring the cannula 40 with elongated members 48 and 50 (as schematically illustrated in FIG. 1), it is possible to form the double cannula 40 from an axially elongated cylindrical member 93 having channels 94 and 96 formed therein and which open to a top surface 95 of member 93. Notably, member 93 has generally parallel side surfaces 97 and 98 which can be spaced apart substantially the same distance as are the side surfaces 44 and 46 on the double cannula 40 illustrated in FIG. 1.

As shown in FIG. 13, forming the double cannula 40 from an elongated cylindrical member permits the channels 94 and 96 to have substantially the same width as channels 54 and 56 of members 48 and 50, respectively, while offering an advantageously greater depth than that afforded by the channels 54 and 56 in the first embodiment described above. Accordingly, in the embodiment shown in FIGS. 11 and 13, and because of the additional depth provided to the channels 94 and 96, an endoscope and an additional surgical instrument can be arranged in vertical overlying relation to each other in either channel 94 and 96 and allowed to extend endwise therethrough.

As schematically illustrated in FIG. 11, the cylindrical member 93 is provided with an apertured tie 99 at that end of member 93 adjacent to the handle 12. As shown in FIG. 11, tie 99 preferably defines a transversely elongated slot 100 that opens to both channels 94 and 96. Moreover, it is important to note, that the elongated cylindrical member 93 can be releasably secured to the handle 12 in a manner substantially similar to the manner by which members 48 and 50 are releasably secured to the handle 12. Thus, no further description need to be provided thereto. Additionally, the distal end of the cylindrical member 93 is provided with a blunt preferably semi-spherical configuration.

Another embodiment of a medical instrument is illustrated in FIGS. 14 through 18. This alternative embodiment of medical instrument is represented in FIGS. 14 and 15 in its entirety by reference numeral 110. The medical instrument 110 is substantially similar to the embodiment of the medical instrument 10 described above with reference to FIG. 1. The elements of the second embodiment of the medical instrument 110 that are identical or functionally analogous to those of the first embodiment of the medical instrument 10 are designated by reference numerals identical to those used for the first embodiment with the exception that the second embodiment reference numerals are in the one-hundred series.

The medical instrument 110 includes an elongated handle 112 with a surgical instrument 114 arranged in releasable association with the handle 112 such that the handle can extend from either side of the surgical instrument. In this embodiment of the invention, surgical instrument 114 is intended to be disposable while the handle 112 is intended to be reusable. Accordingly, the surgical instrument 114 is formed from a material such as polycarbonate or other material that is suitable for the intended purpose and yet is not so expensive that it would not be cost effective to make the surgical instrument 114 disposable.

As shown, handle 112 has elongated configuration that extends generally perpendicular or normal to the longitudinal axis of the surgical instrument 114. Handle 112 is preferably formed from a reusable and sterilizable material such as stainless steel, titanium or the like that may be coated or plated in a manner permitting reuse of the handle 112. Handle 112 includes a body 116 having a top surface 118, a bottom surface 120, a front face 122 and a rear face 124. Preferably, body 116 further defines a grip portion 126 at that end opposite to the end of body 116 to which the surgical instrument 114 releasably attaches. As shown, grip portion 126 is substantially similar to grip 26 discussed above. Suffice it to say, grip portion 126 is ergonomically configured to facilitate a key pinch hold on the medical instrument 110 thus rendering it stable.

In the embodiment of the invention illustrated in FIGS. 14 and 15, the surgical instrument 114 releasably secured to the handle 112 is configured as a double channeled cannula 140. Cannula 140 is substantially similar to cannula 40 described above. Suffice it to say, cannula 140 is formed from a polycarbonate or similar material such that cannula 140 may be considered disposable. Alternatively, the cannula 140 could be formed of rigid clear acrylic or clear plastic to enable the surgeon to visualize structures within the carpal canal. Cannula 140 further includes an apertured tie 158 similar to and serving the same purpose as tie 58 described above. Tie 158 defines a transverse slot 159 that permits access to the dual channels of cannula 140.

Figure 16:
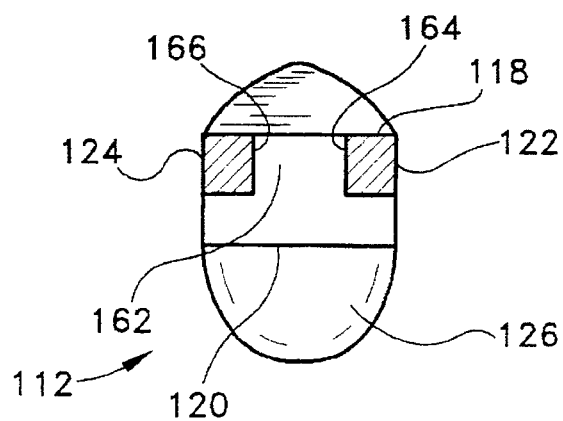
FIG. 16 is a sectional view taken along line 16—16 of FIG. 15.

A locking mechanism 160 secures the handle 112 and the relatively low cost cannula 140 to each other. As will be appreciated, locking mechanism 160 can take a myriad of shapes and configurations without detracting or departing from the spirit and scope of the present invention. In the illustrated embodiment, and as shown in FIGS. 15 and 16, locking mechanism 160 includes a vertical throughbore 162 provided at that end of handle 112 opposite from the grip portion 126. Notably, bore 162 has a closed margin defined by body 116 of handle 112. In the illustrated embodiment, bore 162 has a rectangular cross-sectional configuration and extends between the top surface 118 and a lower surface on body 116 of handle 112. In the embodiment shown, bore 162 defines a first pair of opposed and generally parallel side surfaces 164 and 166 and a second pair of generally parallel and opposed side surfaces 168 and 170.

Figure 17:
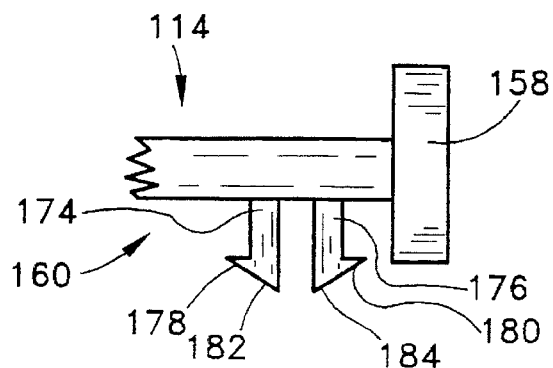
FIG. 17 is a fragmentary side elevational view of an end portion of a surgical instrument forming part of the medical instrument.
Figure 18:
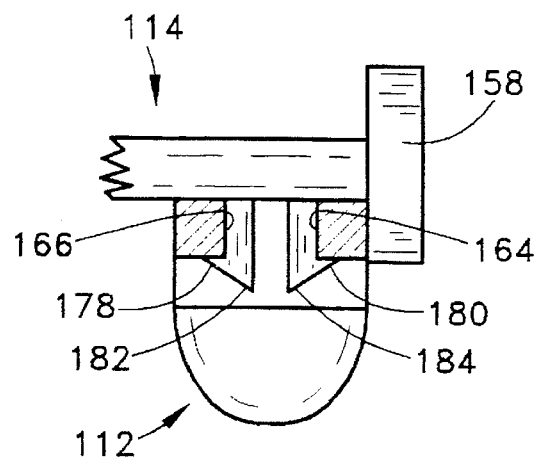
FIG. 18 is a fragmentary side elevational view, with parts broken away, to show the releasable securement of a surgical instrument to a handle of the medical instrument.

As shown in FIGS. 15 and 17, locking mechanism 160 further includes a pair of resiliently biased and axially spaced arms 174 and 176 that are rigidly attached to and depend from an underside of the cannula 140 in axially spaced relation from the tie 158. The arms 174 and 176 are axially spaced apart substantially by the extent of the opening between walls 164 and 166 of bore 162. The thickness of the arms 174 and 176 generally corresponds to the extent of the opening between walls 168 and 170 of bore 162. Thus, the cannula 140 is inhibited from moving in any direction once the arms 174 and 176 are affixed in the opening of bore 162.

Preferably, locking tabs comprising axial extensions 178 and 180 are formed toward the distal ends of arms 174 and 176, respectively. At their widest location, the tabs 178 and 180 are axially spaced from each other somewhat in excess of the extent of the opening between walls 164 and 166 of bore 162. The axial extensions or locking tabs 178 and 180 on arms 174 and 176, respectively, decrease in their axial direction toward their leading edge to define a pair of ramps 182 and 184 thereon. The leading edges of the extensions 178 and 180 are spaced apart a distance somewhat less than the extent of the opening between the walls 164 and 166 of the bore 162 such that after the locking tabs 178 and 180 endwise pass the lower parameter of the bore 162, the arms 174 and 176 resiliently snap outwardly to releasably lock the cannula 140 to the handle 112. As will be appreciated, the locking tabs 178 and 180 at the ends of arms 174 and 176, respectively, inhibit vertical displacement of the cannula 140 relative to the handle 112.

Figure 19:
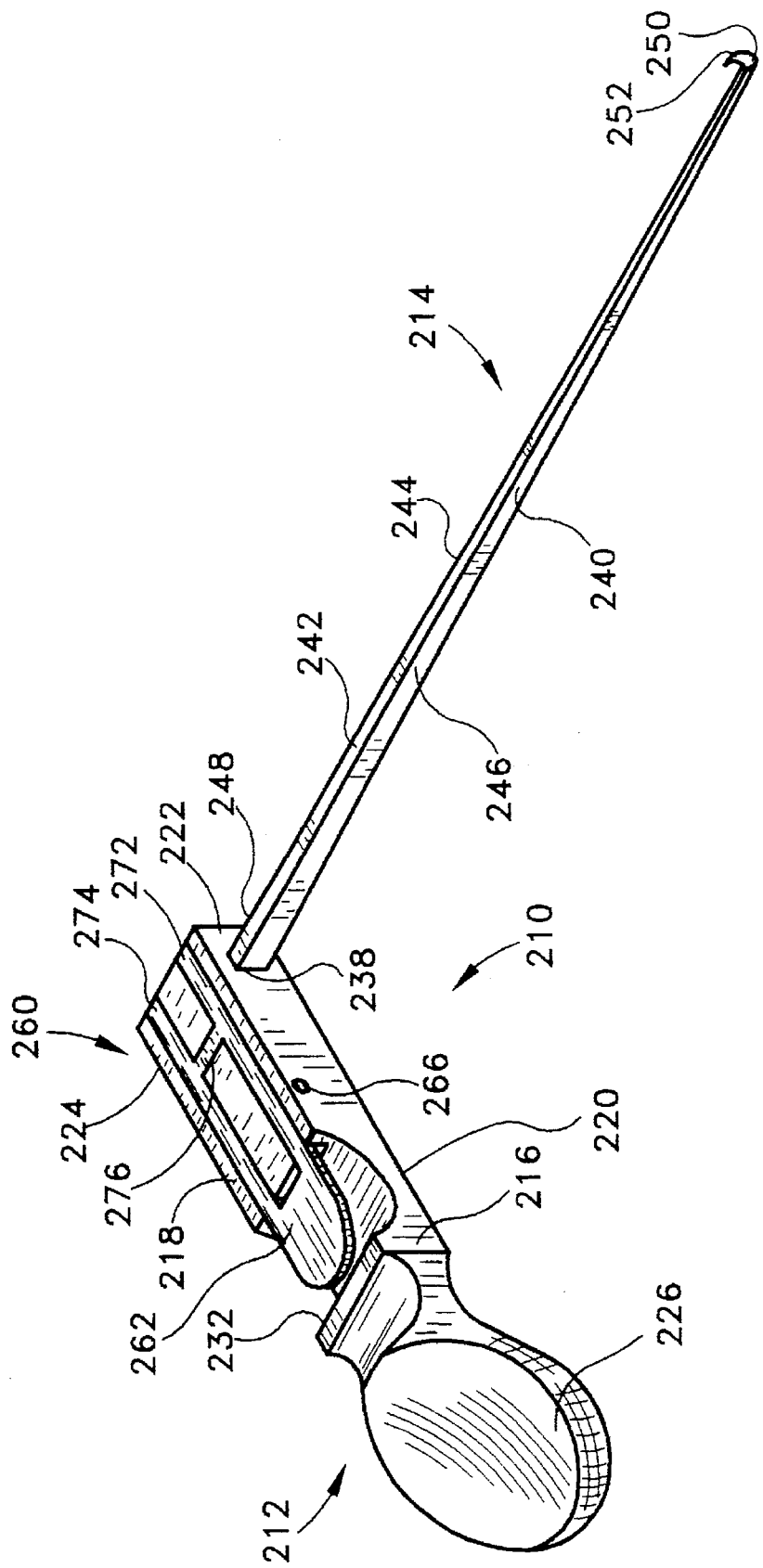
FIG. 19 is a perspective view of an alternative form of the present invention.

Another embodiment of a medical instrument is illustrated in FIG. 19 and is generally represented in its entirety by reference numeral 210. The medical instrument 210 is similar to the embodiment of the medical instrument 10 described above with reference to FIG. 1. The elements of this embodiment of the medical instrument 210 that are identical or functionally analogous to those of the first embodiment of the medical instrument 10 are designated by reference numerals identical to those used for the first embodiment with the exception that the reference numerals for this embodiment of the invention are in the two-hundred series.

Figure 20:
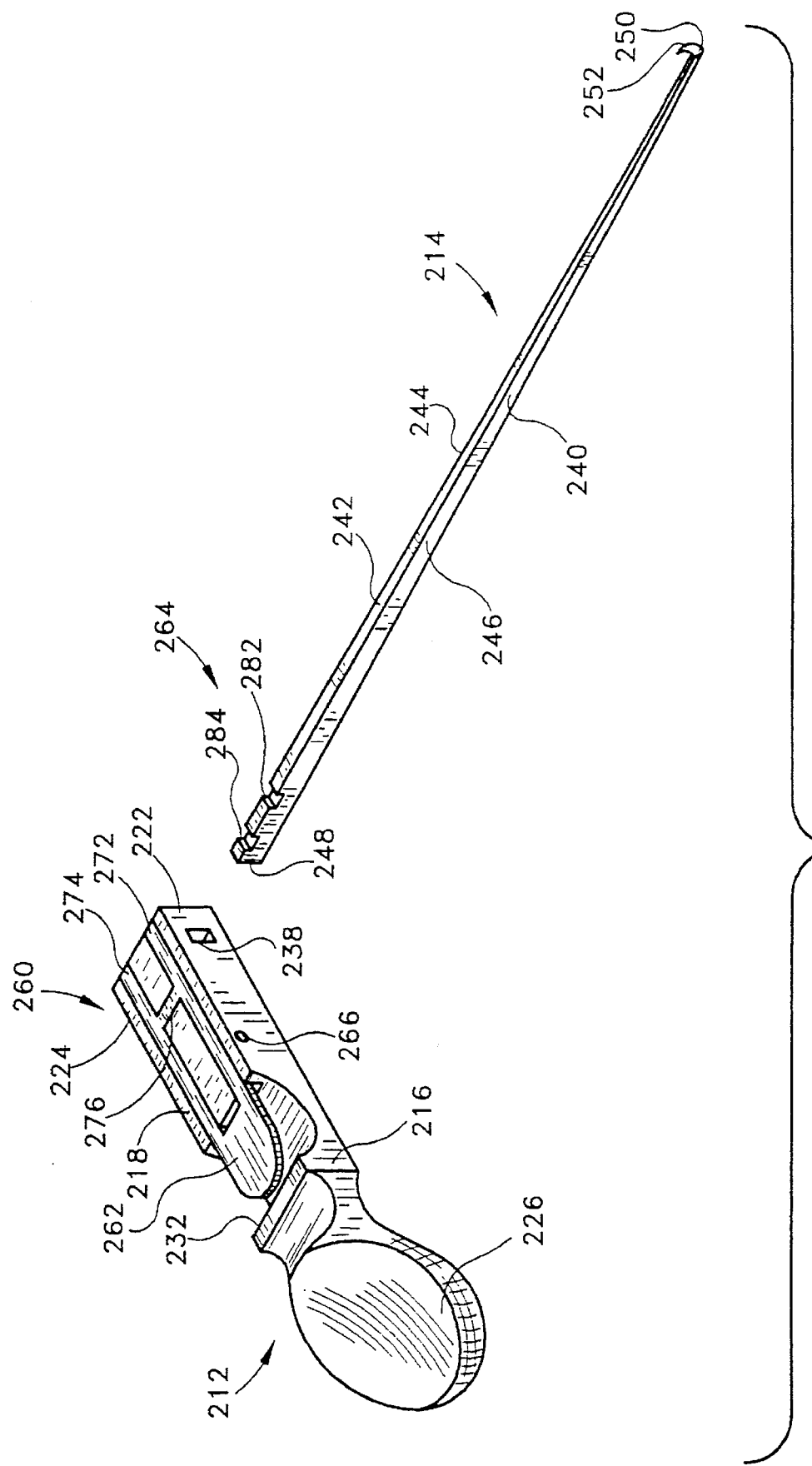
FIG. 20 is a perspective view similar to FIG. 19 but showing components of the carpal tunnel medical instrument in disassembled or released relationship relative to each other.
Figure 21:
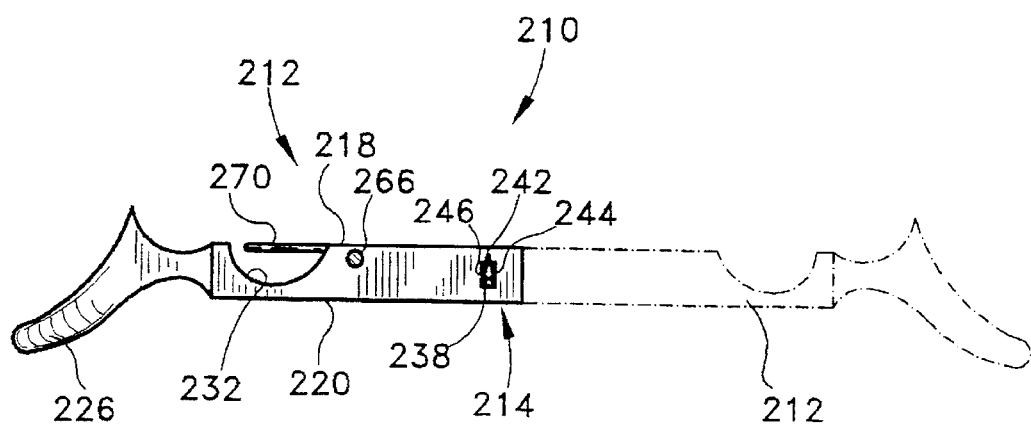
FIG. 21 is a front elevational view of the medical instrument schematically illustrated in FIG. 19, with a phantom line showing of a handle of the instrument in an alterative position.

The medical instrument 210 includes an elongated handle 212 with the surgical instrument 214 arranged in releasable association with the handle 212. As shown, handle 212 has an elongated configuration that extends generally perpendicular or normal to the longitudinal axis of the surgical instrument 214. Handle 212 includes a body 216 having a top surface 218, a bottom surface 220, a front face 222 and a rear face 224. Preferably, body 216 further defines a grip portion 226 at that end opposite to the end of body 216 to which the surgical instrument 214 releasably attaches. Suffice it to say, grip portion 226 is ergonomically configured to facilitate a key pinch hold on the medical instrument 210 thus rendering its stable. As shown in FIGS. 19, 20 and 21, the top surface 218 of body 216 is further configured with a convex recess 232 extending between the front and rear face as 222 and 224, respectively, and adjacent or proximate to the grip portion 226.

Figure 22:
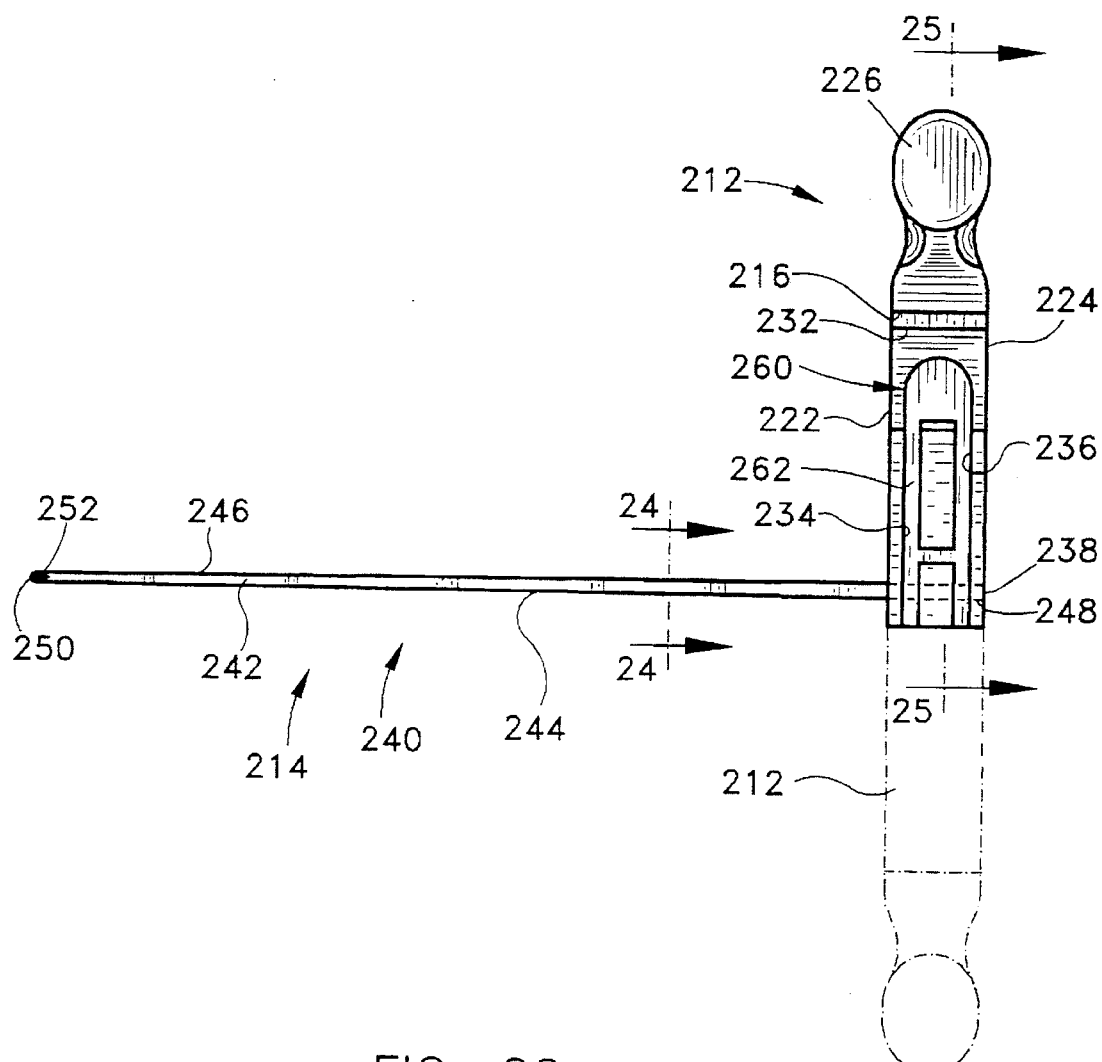
FIG. 22 is a plan view of the medical instrument schematically illustrated in FIG. 19, with a phantom line showing of a handle of the instrument in an alterative position.
Figure 23:
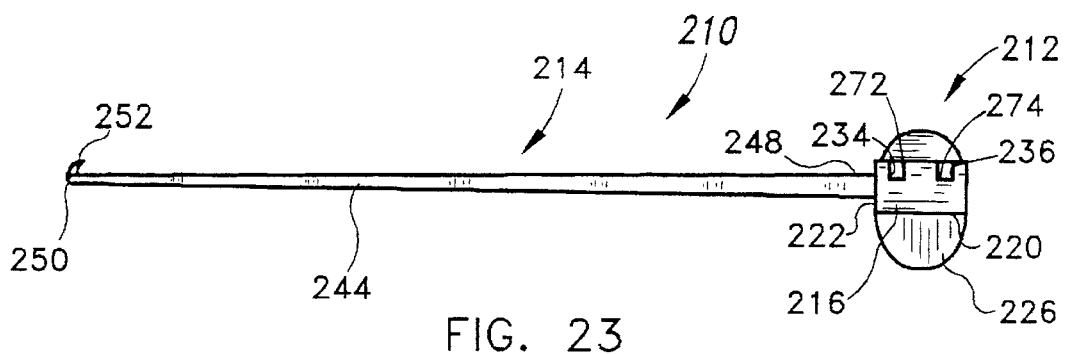
FIG. 23 is a side elevational view of the medical instrument schematically illustrated in FIG. 19.

Turning to FIG. 22, at that end opposite from the grip portion 226, the top surface 218 of body 216 is configured with a pair of spaced apart generally parallel vertical recesses or channels 234 and 236. For purposes to be described hereinafter, each channel or recess 234, 236 opens to the end of body 216 and to the top surface 218 of handle 212.

At that end opposite from the grip portion 226, body 216 of handle 212 further defines a throughbore or hole 238 that extends between and preferably opens to both the front and rear faces 222 and 224, respectively, of body 216. Notably, the transverse hole or throughbore 238 has a closed margin that is defined totally by body 216 of handle 212. Furthermore, it should be noted, that the upper margin of the throughhole 238 is disposed above the lowermost edge of both channels 234 and 236. As such, channels 234, 236 each intersect with and open to the throughbore 238.

In the embodiment of the invention illustrated in FIGS. 19 through 22, the surgical instrument 214 releasably secured to the handle 212 is a cutting blade 240. Blade 240 is preferably formed from a suitable rigid material such as stainless steel to promote sterilization and reuse of the blade. As shown, blade 240 includes a top surface 242 and a pair of opposed generally parallel side surfaces 244 and 246 (FIG. 22). Blade 240 further defines first and second generally axially-aligned ends 248 and 250, respectively. The first end 248 of blade 240 releasably fits into the bore 238 on the handle 212 and is releasably secured to the handle 212 in a manner preventing endwise displacement of the blade 240 after it is releasably secured to the handle 212. The second or opposite end 250 of blade 240 is preferably configured with a cutting instrumentality 252 that extends upwardly from the top surface 242 of the blade 240.

Figure 24:
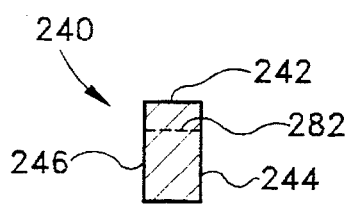
FIG. 24 is a sectional view taken along line 24—24 of FIG. 22.

As schematically illustrated in FIG. 24, blade 240 preferably has a generally rectangular cross-sectional configuration extending away from at least the first end 248 of the blade 240 toward the second end 250. The throughbore 238 in the handle 212 is provided with a configuration that corresponds to the cross-sectional configuration of that portion of the blade 240 extending through the handle 212 whereby the blade 240 is stabilized once it is secured in the handle 212. As will be appreciated by those skilled in the art, other cross-sections besides the rectangular cross-sectional configuration illustrated in the drawings would equally suffice without detracting or departing from the spirit and scope of the present invention.

In that embodiment of the invention where handle 212 and the surgical instrument 214 are releasably secured to each other, a manually operated locking mechanism 260 is provided to releasably secure the handle 212 and surgical instrument 214 to each other. In the embodiment illustrated in FIGS. 23 through 26, the locking mechanism 260 includes a locking lever 262 preferably carried by the handle 212 and which cooperates and combines with a locking apparatus 264 (FIG. 20) provided on the surgical instrument 214 to releasably secure the instrument 214 and the handle 212 to each other.

Figure 25:
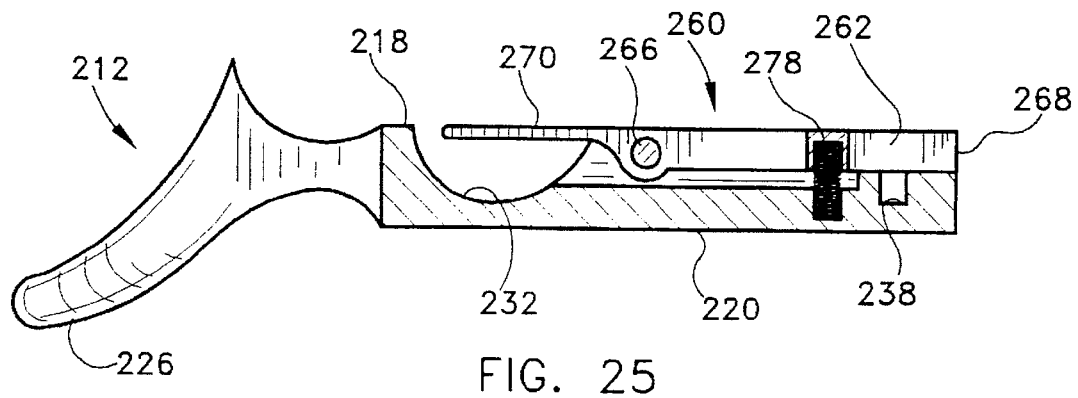
FIG. 25 is a sectional view taken along line 25—25 of FIG. 22.

As shown in FIGS. 19, 20, 25 and 26, the locking lever 262 of locking mechanism 260 is mounted toward the top surface 218 of the handle 212. More specifically, lever 262 is mounted in a fulcrumed manner to the body 216 of handle 212 preferably by a pivot pin 266 arranged intermediate first and second ends 268 and 270 of the lever 262. In the illustrated embodiment, locking lever 262 has generally U-shaped planar configuration including a pair of generally parallel fore-and-aft spaced arms 272 and 274 that extend away from the first end 268 of the lever 262 and are permitted to move vertically within the channels or recesses 234 and 236, respectively, defined by body 216 of the handle 212 in response to rocking movement of the lever 262 about pivot pin 266. As shown in FIGS. 19 and 20, arms 272 and 274 are preferably rigidly joined to each other intermediate their ends by a brace 276. As shown in FIG. 25, a tension spring 278 is carried between body 216 of handle 212 and lever 262. The purpose of spring 278 is to resiliently bias the locking lever 262 toward a locked or closed position.

Figure 26:
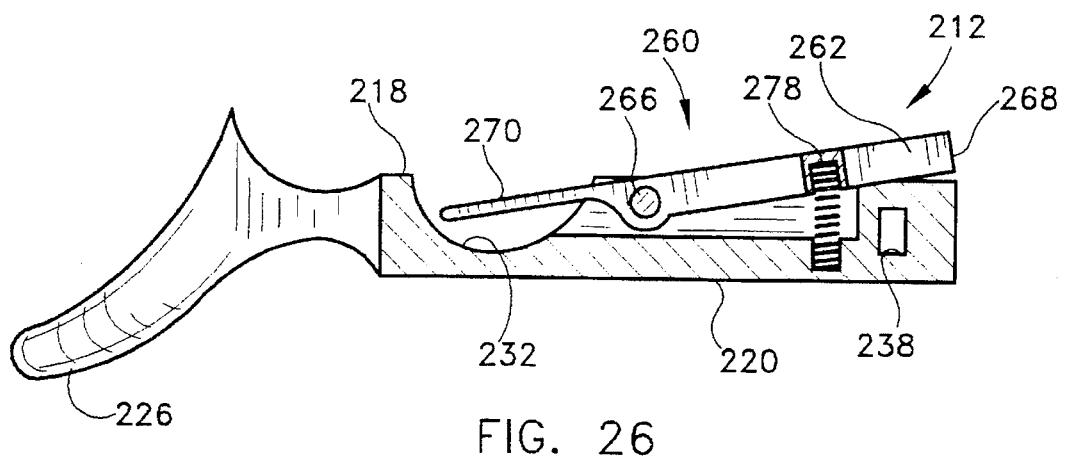
FIG. 26 is a sectional view similar to FIG. 25 but showing a locking mechanism in a released condition.

At the second end 270, the locking lever 262 is designed for manual engagement. As shown in FIGS. 20, 21, and 26, the second end 270 of locking lever 262 terminates in the area above the recess 232 defined in the body 216 of handle 212. As will be appreciated, the recess 232 provides adequate space to allow the free second end 270 of the locking lever 262 to be vertically displaced against the action of spring 278 thus resulting in rocking movement of the locking lever 262 about the axis of pivot pin 266.

As shown in FIG. 20, the first end 248 of blade 240 defines a pair of axially-spaced notches 282, 284 defined on and extending across the top surface 242 of the blade 240. The notches 282, 284 on blade 240 are axially-spaced apart a distance corresponding to the distance separating arms 272, 274 on locking lever 262. The arms 272, 274 on locking lever 262 and notches 282, 284 on the surgical instrument 214 are configured to fit one within the other when arms 272, 274 are arranged in locking engagement with the surgical instrument 214. Once the blade 240 is properly endwise positioned within the bore 238 on handle 212, the arms 272, 274 on the spring-biased locking lever 262 fit within the recessed notches 282, 284 on the blade 240 thereby positively locking the blade 240 in place and thus preventing endwise movement of the blade 240 relative to the handle 212.

As will be appreciated, release of the locking mechanism 260 is readily and easily affected by merely pressing downwardly on the second end 270 of the locking lever 262 against the action of spring 278. As shown in FIG. 26, application of a downwardly directed force on the second end 270 of the locking lever 262 results in rocking movement of the locking lever 262 about pivot pin 266. Thus, the locking relationship between the locking lever 262 and the blade 240 is released thus allowing the blade 240 to be easily and readily removed from the handle 212 to facilitate and promote disassembly of the medical instrument 210 by separating handle 212 from the surgical instrument 214.

As discussed with respect to the first embodiment, releasably attaching the handle 212 and surgical instrument 214 to each other allows the handle 212 to be moved to either side of the instrument 214 while maintaining the operative relationship of the instrument 214 and the handle 212. That is, when the handle 212 is positioned as shown in FIGS. 19 and 20, the handle 212 extends perpendicular to and outwardly from the side surface 246 of the blade 240, with the top surface or side 218 of handle 212 having a predetermined relationship relative to the top surface 242 of the blade 240. Turning now to FIG. 27, when the handle 212 is shifted or moved to a second or alternate position such that the handle 212 extends from side surface 244 of blade 240 rather than from side 246, the handle 212 remains perpendicular to and extending outwardly from the side surface 244 of the blade 240. It is important to note, however, that although shifted to the opposite side of the blade 240, the top side or surface 218 of the handle 212 remains in the same predetermined orientation or relation relative to the top surface 242 of blade 240.

Different forms of surgical instruments can advantageously be releasably secured to the handle 212 of the medical instrument 210. Rather than being configured as blades, however, and as schematically represented in FIG. 28, the surgical instrument 214 can be configured as a probe or nerve hook. The probe or surgical instrument, schematically represented in FIG. 28, is represented in its entirety by reference numeral 340 and is formed from a suitable rigid material, preferably stainless steel, although other materials, i.e., titanium, would likewise suffice without detracting or departing from the spirit and scope of the present invention.

As shown in FIG. 28, probe 340 has a top surface 342 extending between first and second axially aligned ends 348 and 350, respectively. At least at the first end 348, the cross-sectional configuration of probe 340 substantially corresponds to that of blade 240 discussed in detail above. The first end 348 of probe 340 further includes a pair of axially spaced notches 382 and 384 that are identical to and serve the same purpose as notches 282 and 284 on blade 240 discussed above. At the second end 350, probe 340 is provided with an instrumentality 352 that projects upwardly and away from the top surface 342 of the probe 340. The purpose of the instrumentality 352 is to apply a displacing force to human structures that obfuscate the operative field of view during a carpal tunnel release surgical procedure.

An alternative embodiment of a surgical instrument or probe is schematically illustrated in FIG. 29. This alternative probe or nerve hook is represented in its entirety by reference numeral 340A. Probe 340A substantially corresponds to probe 340 but is of a different length. Otherwise, probes 340 and 340A are identical in structure and can be interchangeably and releasably secured to the handle 212 of the medical instrument 210.

Figure 30:
FIGS. 30 and 31 are schematic enlarged side elevational views of rasps that can be used in combination with the medical instrument schematically illustrated in FIGS. 19 through 27.
Figure 31:
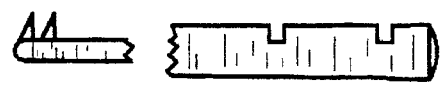
Figure 32:
FIGS. 32 through 37 are schematic enlarged side elevational views of different forms of cutting blades that can be used in combination with the medical instrument schematically illustrated in FIGS. 19 through 27.
Figure 33:
Figure 34:
Figure 35:
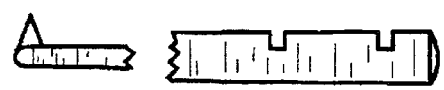
Figure 36:
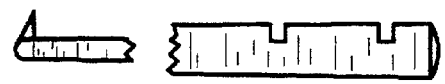
Figure 37:

FIGS. 30 and 31 schematically illustrate rasps that are releasably connectable to the handle 212 and are interchangeable with the probes 340, 340A or blade 240. The rasps, schematically shown in FIGS. 30 and 31, are configured to lockingly interconnect with handle 212 in the same manner as discussed above regarding blade 240.

FIGS. 32 through 37 schematically illustrate alternative blade forms. The blade forms schematically illustrated in FIGS. 32 through 37 substantially correspond to the configuration of blade 240 with the exception that different forms of cutting instrumentalities extend upwardly from a top surface of each blade. Otherwise, the blades shown in FIGS. 32 through 37 are interchangeable with the blade 240 and each blade form schematically illustrated in FIGS. 30 through 37 can be releasably secured to the handle 212 of the medical instrument 210 in substantially the same manner as described with respect to blade 240.

As will be discussed hereinafter, a carpal tunnel medical instrument similar to that shown in FIGS. 1 through 8 is initially inserted through a carpal tunnel surgical opening. To add strength and rigidity to the double cannula 40 inserted through the surgical opening, an obturator 400 is releasably fitted into the channels 54, 56 of the cannula 40. Obturator 400 is preferably formed from stainless steel or other suitable material. As shown in FIG. 38, the obturator 400 includes a pair of elongated parallel and adjacent tubular members 402, 404 that are joined to each other along their lengths. As shown in FIGS. 38, 39 and 40, a handle 406 is attached at one end to the elongated members 402, 404. As will be appreciated, the cross-sectional configuration and length of the tubular members 402, 404 of obturator 400 correspond to and slidably fit within the dual channeled configuration of the double channeled cannula 40. When used in combination with a dual channeled cannula, as schematically represented in FIGS. 11 and 13, the obturator 400 may include an elongated tubular member 410 having a cross-sectional configuration as schematically represented in FIG. 41.

Figure 42:
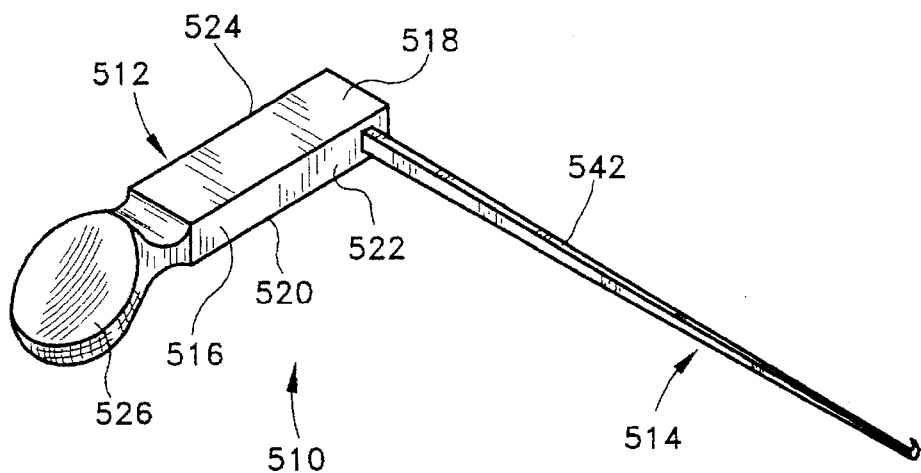
FIG. 42 is a perspective view of still another embodiment of the present invention.
Figure 43:
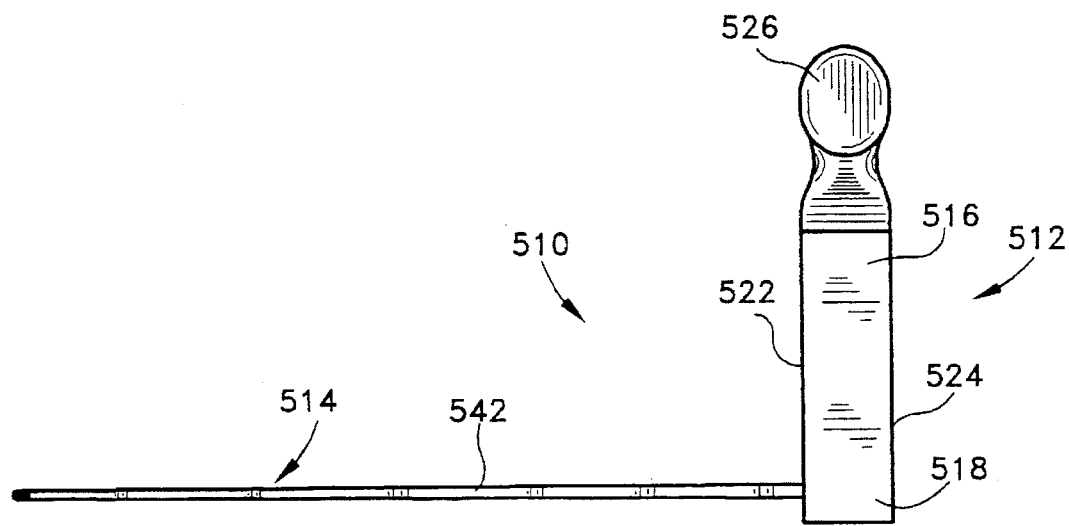
FIG. 43 is a plan view of the embodiment of the invention illustrated in FIG. 42.

Still another embodiment of the invention is schematically represented in FIGS. 42 and 43. This alternative embodiment of the medical instrument is disposable in its entirety and is represented in its entirety in FIGS. 42 and 43 by reference numeral 510. The elements of this carpal tunnel medical instrument that are functionally analogous to that embodiment of the invention schematically illustrated in FIG. 19 are designated by reference numerals identical to those used in FIG. 19 with the exception that the reference numerals for this embodiment of the invention are designated in the five-hundred series.

The medical instrument 510 includes elongated handle 512 and a surgical instrument 514 that are either integrally formed with each other or permanently attached to each other thereby providing a one-piece medical instrument 510. As shown, handle 512 has elongated configuration that extends generally perpendicular or normal to the longitudinal axis of the surgical instrument 514.

Handle 512 preferably includes a body 516 having a top surface 518, a bottom surface 520, a front face 522 and a rear face 524. In the illustrated embodiment, body 516 further defines a grip portion 526 at that end opposite to the end of body 516 from which the surgical instrument 514 extends. Suffice it to say, grip portion 526 is ergonomically configured to facilitate a key pinch hold on the medical instrument 510 thus rendering it stable. Handle 512 of instrument 510 is preferably formed from a material such as polycarbonate or other material which is suitable for the intended purpose and yet is sufficiently inexpensive such that it remains economically feasible to discard the entire carpal tunnel medical instrument 510 following one surgical use.

The surgical instrument 514 associated with the handle 512 can be of any suitable design corresponding to the dual channeled cannula 40, dual cannula 140 schematically illustrated in FIGS. 1 or 11, respectively, or any blade, rasp, probe or nerve hook configuration illustrated in FIGS. 28 through 37. In the illustrated embodiment, and because the instrument 510 is intended to be disposed of following one use, the surgical instrument 514 is preferably formed from stainless steel, titanium or any other suitable material. Notably, the surgical instrument includes a top surface 542. A salient feature of the medical instrument 510 illustrated in FIGS. 42 and 43 is that the handle 512 and surgical instrument 514 are disposed in substantially the same plane extending generally parallel to the top surface 542 of the instrument 514.

Figure 44:
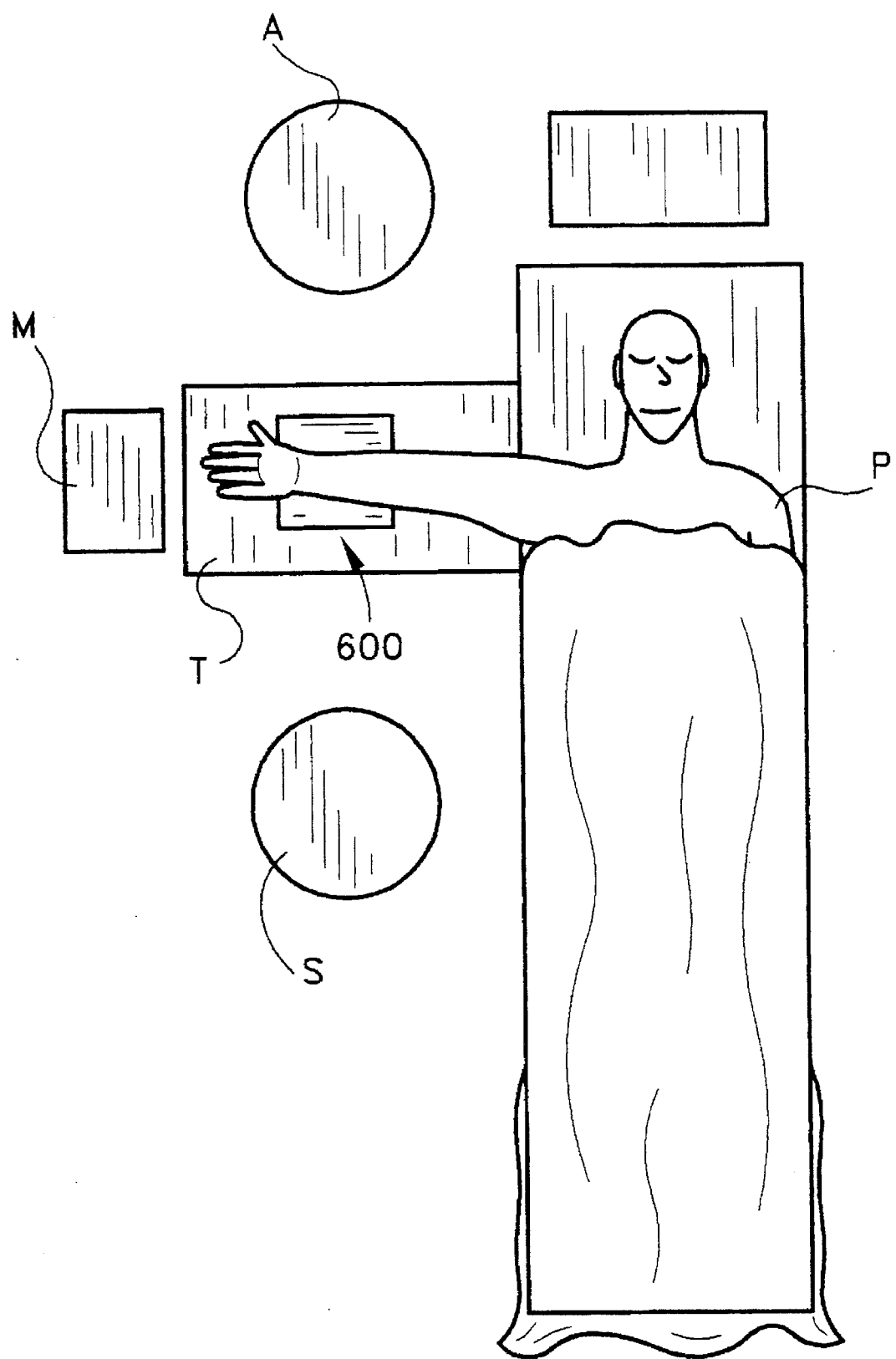
FIG. 44 is a schematic representation of an operating set-up wherein the present invention will find utility.
Figure 46:
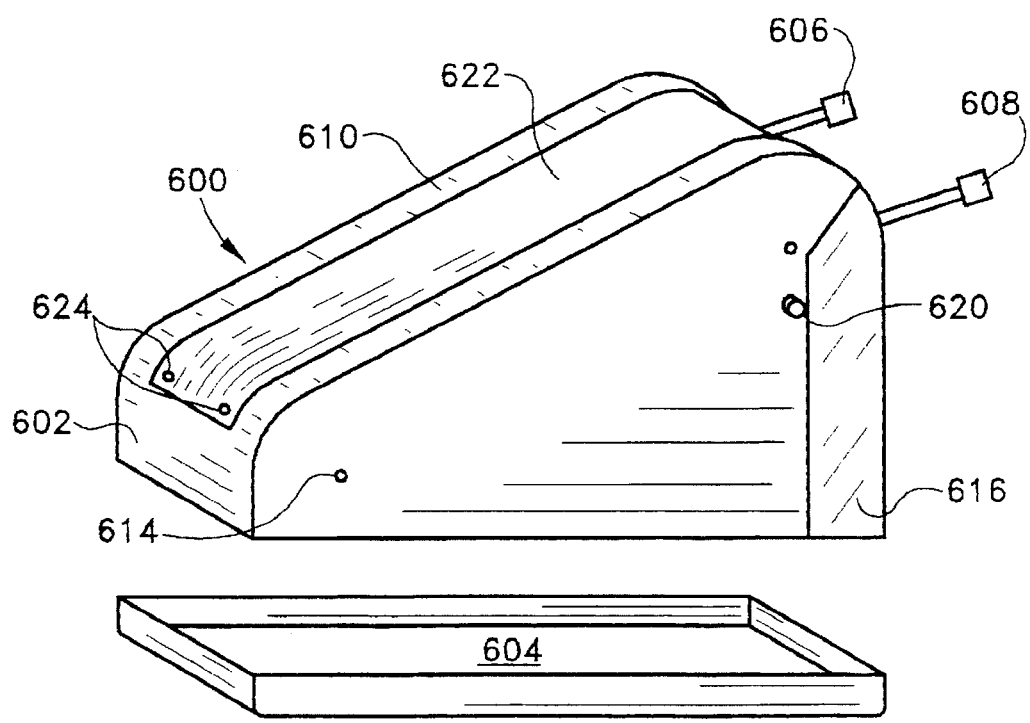
FIG. 46 is a perspective view of a modified hand holder to be used during a carpal tunnel release surgical procedure.
Figure 47:
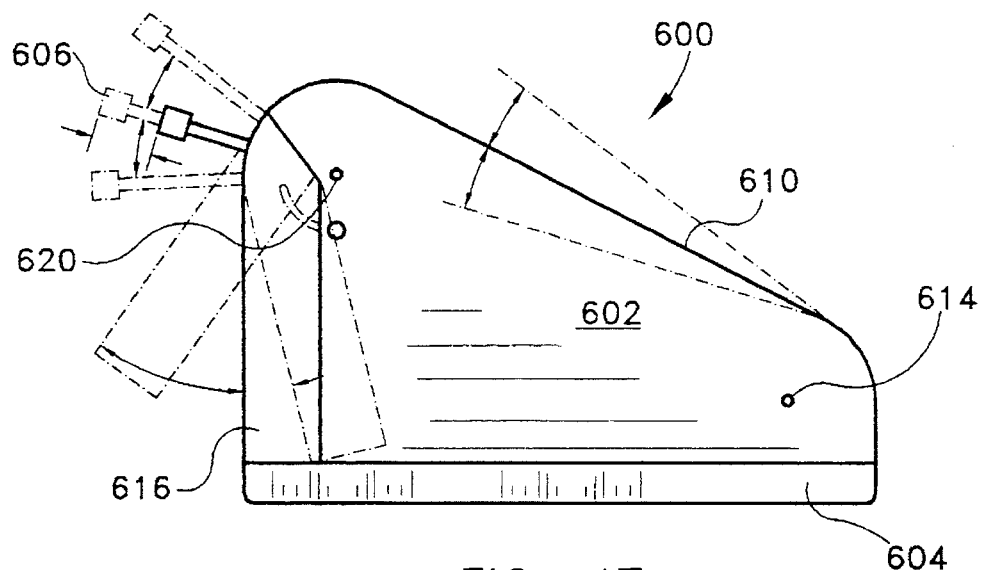
FIG. 47 is a front elevational view of the hand holder illustrated in FIG. 46.
Figure 48:
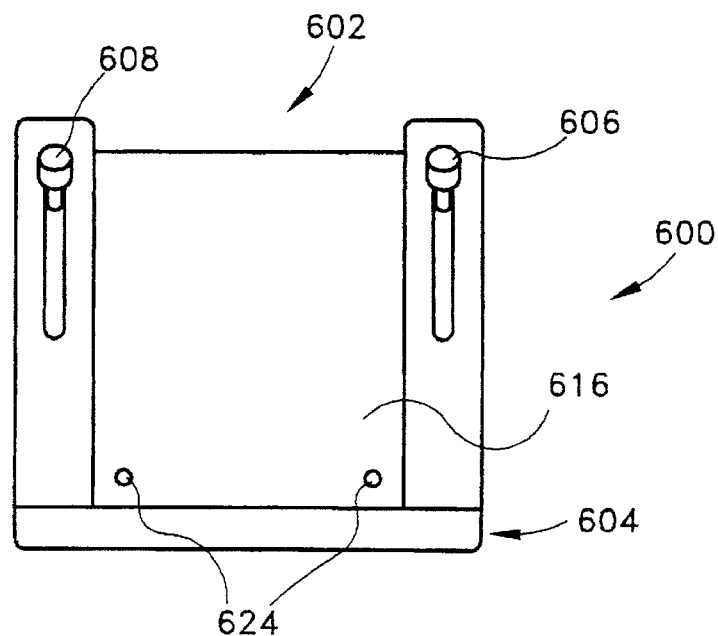
FIG. 48 is a side elevational view of the hand holder illustrated in FIG. 47.

As shown in FIG. 44, the patient P is positioned with the arm abducted 90° and positioned on a handtable T after sterile prepping and draping of the patient. The hand is positioned with the wrist preferably supported and secured on an adjustable hand holder 600 (FIGS. 46, 47 and 48). The surgeon S should be positioned with their operating (dominant) hand proximal with respect to the patient P. The assistant A should sit opposite to the surgeon. If a single video monitor M is used, the monitor is placed directly in line with the end of a handtable T that supports the abducted arm of the patient P. If two monitors are used, they may be positioned behind the assistant A and behind the surgeon S for ease of visualization for both persons.

As shown in FIGS. 46 through 48, the hand holder assembly 600 includes a hand holder 602 that is positioned above and in combination with a surgical instrument tray 604. Preferably, tray 604 is normally disposed beneath holder 602. The hand holder 602 is designed to be adjustable. As shown, finger posts 606 and 608 are arranged in combination with the hand holder 602 and are designed to rotate through a predetermined angle and telescope. A main section 610 of the hand holder 602 is allowed to pivot about a forward pivot 614. A second portion 616 of the hand holder 602 is permitted to pivot about a rearward and second pivot 620. A disposable covering 622 is releasably held to the holder 610 by suitable fasteners 624 as shown in FIGS. 46 and 48.

Figure 45:
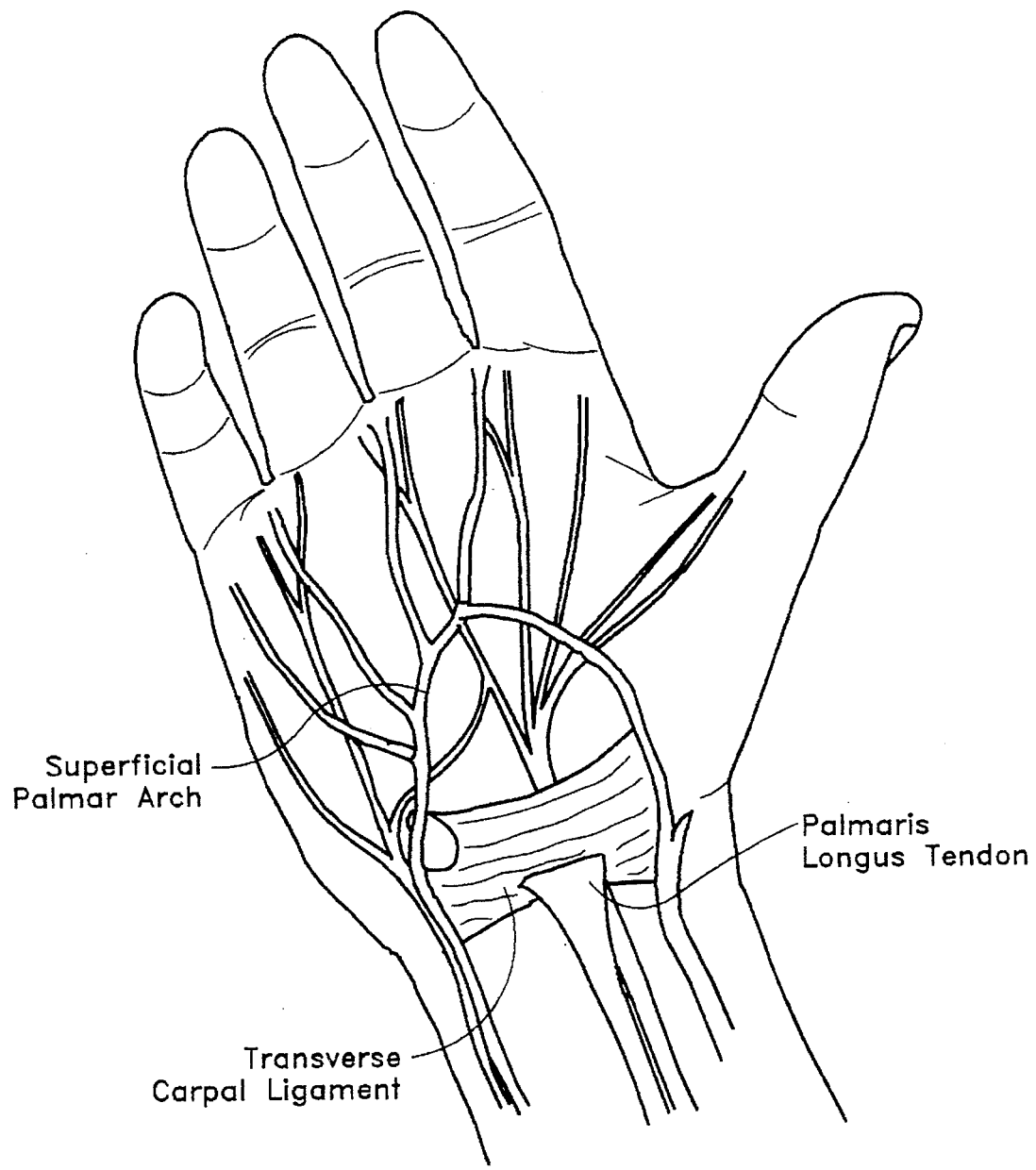
FIG. 45 is a schematic representation of a hand of a patient.

The carpal tunnel release surgical procedure is best performed under arm tourniquet control with local anesthesia. FIG. 45 provides a schematic representation of the hand and surgical area wherein the carpal tunnel release surgical procedure is to be performed. A proximal incision of about 1 cm. is made just to the ulnar border of the palmaris longus tendon, 1 cm. proximal to the most proximal wrist crease. A bipolar electrocautery is preferably used to coagulate rather than tear superficial volar veins. The distal forearm fascia is identified, and released proximally some 4 cm. The proximal margin of the transverse carpal ligament is easily identified, and a subligamentous approach is made to the carpal canal in the axis of the midline of the fourth ray. A plane is developed directly underneath the transverse carpal ligament by teasing away the ulnar bursa as best as possible prior to introduction of the dual channelled cannula 40.

Figure 49:
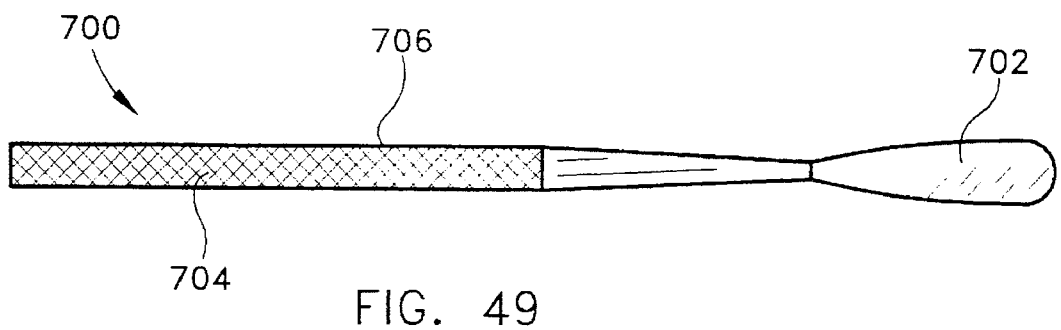
FIG. 49 is a plan view of a handle used during a carpal tunnel release surgical procedure.
Figure 50:
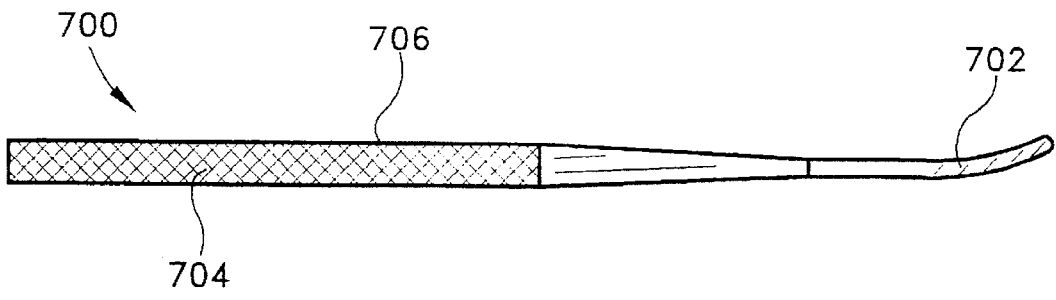
FIG. 50 is a front elevational view of the handle illustrated in FIG. 49.

As shown in FIGS. 49 and 50, a handle 700 is inserted into the incision and is used to tease away and free the bursa prior to insertion of the double channeled cannula 40 into the incision. As shown in FIGS. 49 and 50, handle 700 has a configured operating end 702 and a handle end 704. A textured outer surface 706, i.e., knurling, is provided along the outer surface of the handle end 704 extending toward the operating end 702. The purpose of the textured surface 706 is to provide the surgeon S with a positive grip on the handle 700.

Figure 54:
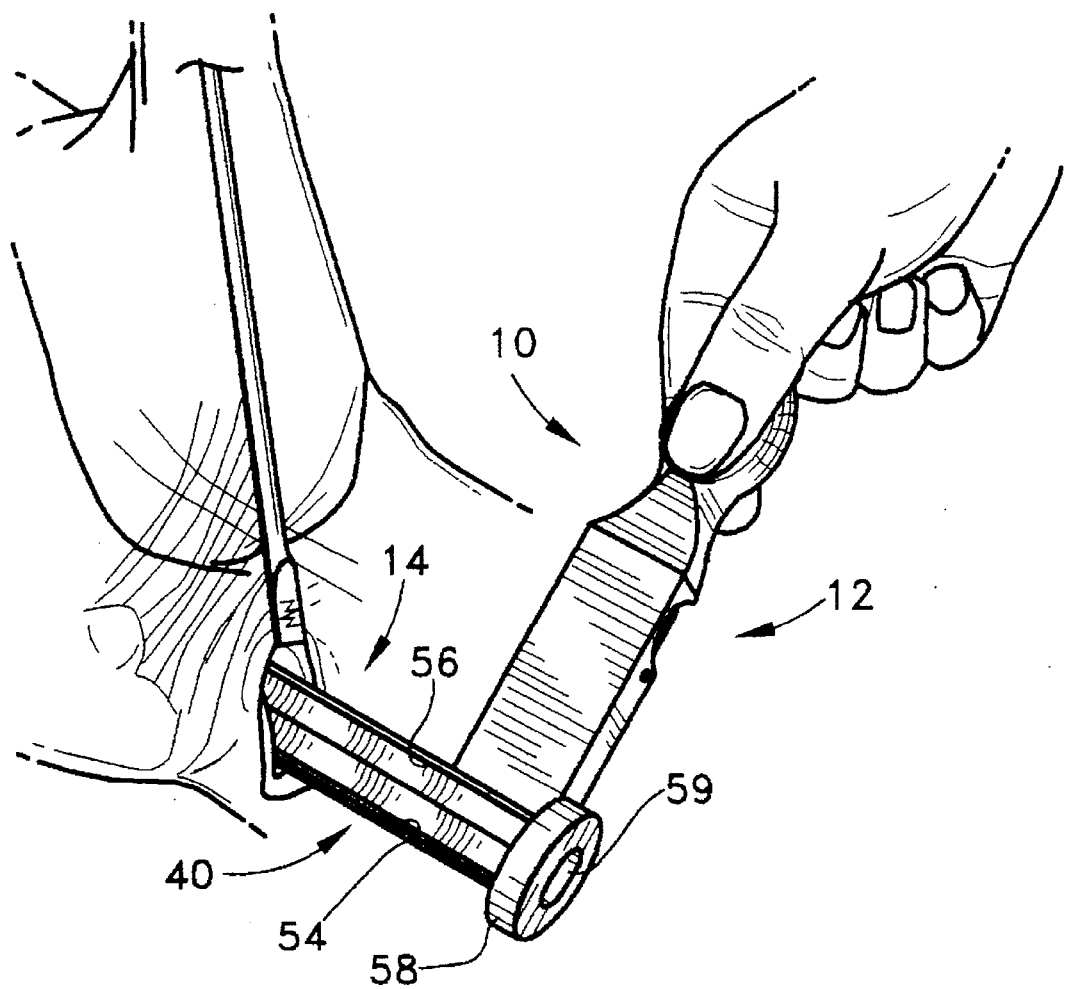
FIG. 54 is a schematic representation of the medical instrument according to the present invention being used during a two-handed carpal tunnel release surgical procedure.

As shown in FIG. 54, a medical instrument as shown in FIGS. 1 through 8 is now inserted through the incision. As will be appreciated, alternative embodiments of the cannula 40 could likewise be inserted in the manner schematically illustrated. Since the alternative embodiments of the cannula 40, however, are functionally analogous to the cannula 40, only cannula 40 will be described with the understanding that the alternative embodiments could likewise be used without detracting or departing from the spirit and scope of the present invention.

The obturator 400 is placed in the dual channeled cannula 40 to give it greater rigidity and ease of insertion. Care should be taken during the insertion of the cannula 40 to maintain the top surface 42 of the cannula directed volarward against the undersurface of the transverse carpal ligament. Moreover, care should be taken to avoid passing the double-channelled cannula 40 an excessive distance into the palm to avoid injury to the distal neurovascular structures. The cannula 40 is endwise inserted until the distal or blunt end of the cannula 40 extends to the distal margin of the transverse carpal ligament. The transverse carpal ligament is easily palpable and ascertained by the feeling of "giving way" when the most distal margin of the transverse carpal ligament is passed by the blunt end of the cannula. The obturator 400 is then removed, and the right angle handle or holder 12 is attached to the cannula 40 to face away from the surgeon S and is held by the assistant A.

Figure 55:
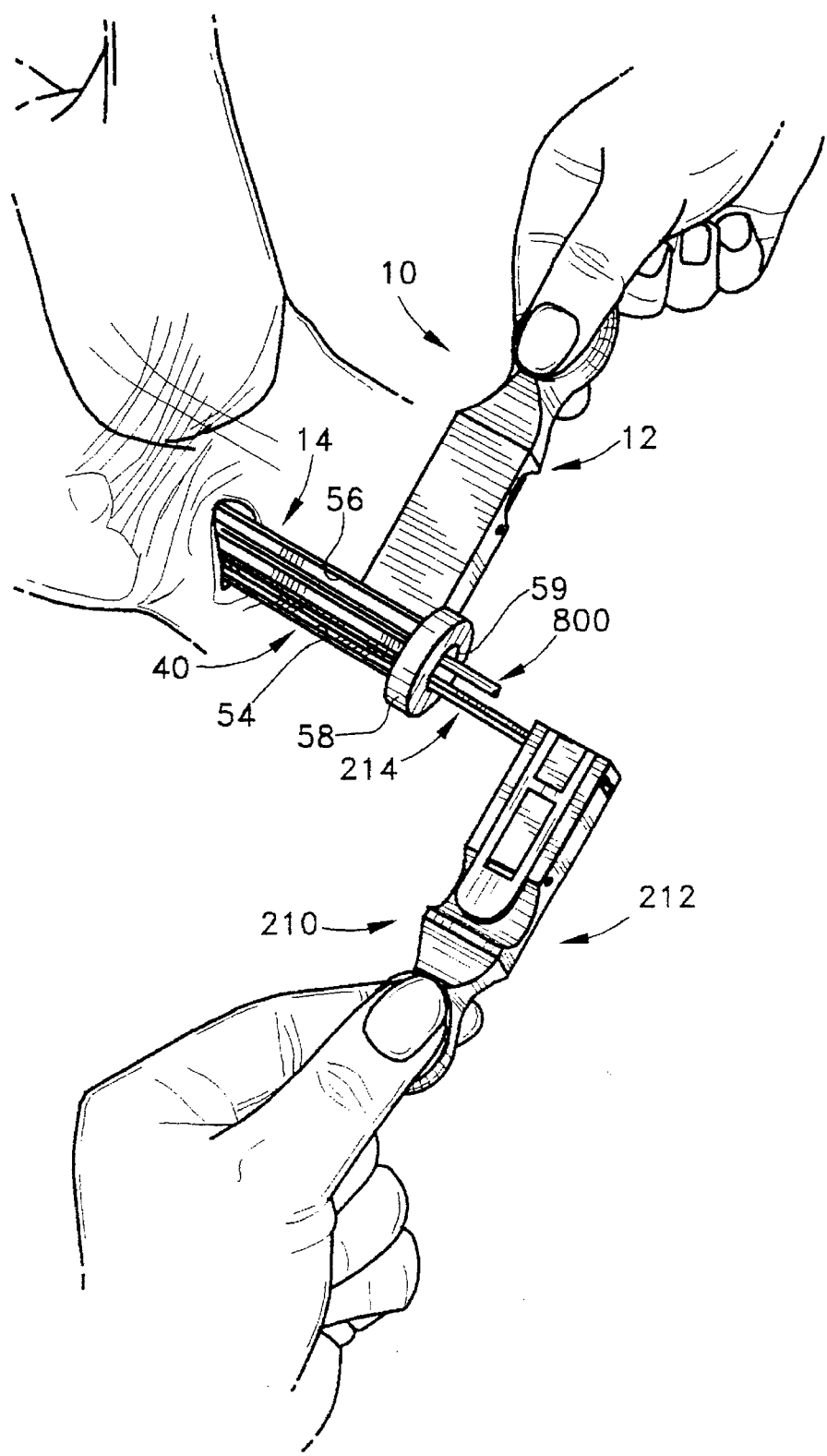
FIG. 55 is a view similar to FIG. 54 but showing an advanced step during the two-handed carpal tunnel release surgical procedure.

As schematically illustrated in FIG. 55, a 2.3 mm. or smaller, preferably modified, endoscope 800 (FIGS. 51 through 53) is now inserted through the opening 59 in tie 58 and into channel 56 in the cannula 40 when operating on a patient's right hand. As will be appreciated, in the alternative form as shown in FIG. 10, endoscope 800 will be inserted into channel 54 of the cannula 40 when operating on a patient's left hand. Notably, channels 54, 56 in cannula 40 provide an unobstructed passage for the endoscope 800 to allow the underside of the transverse carpal ligament to be easily visualized and identified on the monitor M.

Figure 51:
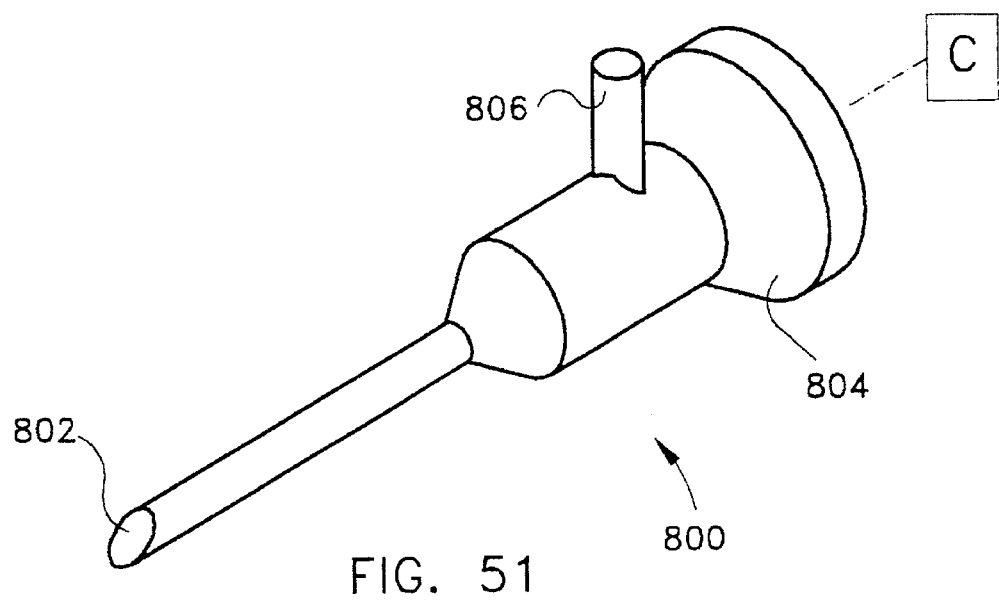
FIG. 51 is a schematic perspective view of a modified endoscope to be used during the carpal tunnel surgical procedure.
Figure 52:
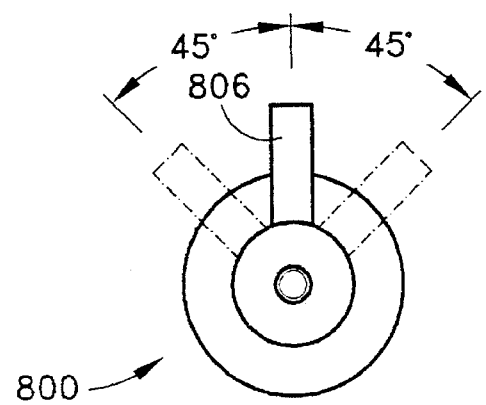
FIG. 52 is a side elevational view of the modified endoscope illustrated in FIG. 51.
Figure 53:
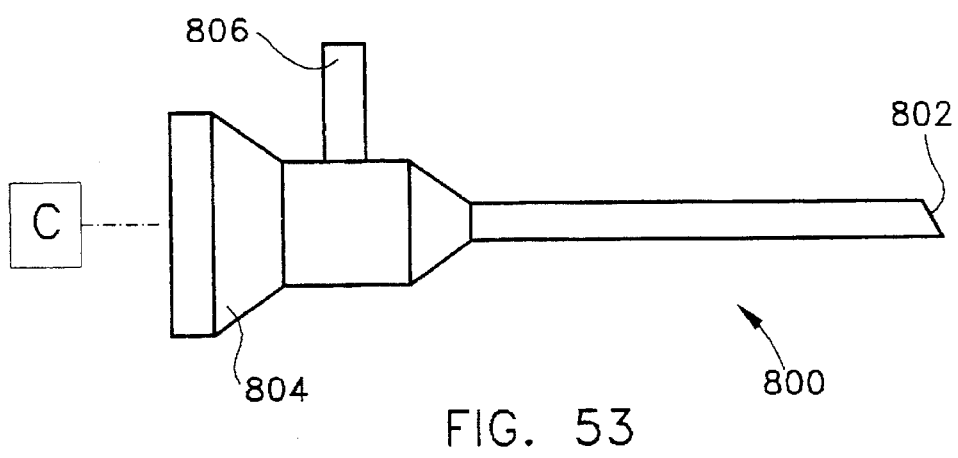
FIG. 53 is a front elevational view of the endoscope illustrated in FIG. 52.

FIGS. 51, 52 and 53, schematically illustrate a modified endoscope 800 having a scope length of about 15 mm. As is conventional, the modified endoscope 800 has an elongated configuration that terminates at a free end 802. End 802 of endoscope 800 has about a 30 degree look-up. At the opposite end 804, the endoscope 800 is attached in a well known manner to a suitable camera C. Intermediate the ends thereof, endoscope 800 has a light source 806 that extends upwardly at about a 90 degree angle relative to the longitudinal axis of the endoscope 800. As shown in FIG. 52, the endoscope is preferably configured such that the light source 806 can be rotated or swiveled through about a 90 degree angle thus removing the light source 806 from or at least improving the relationship of the light source 806 relative to the surgeon's S operating field. In the illustrated embodiment, the light source swivels about 45 degrees to each side of a generally vertical plane passing through the longitudinal axis of the modified endoscope 800.

In an alternate form, the camera end 804 may be disposed at a variably acute angle relative to the longitudinal axis of the endoscope, to maximally remove it from the surgeon's operative field, but still enable the surgeon to manipulate it.

Figure 56:
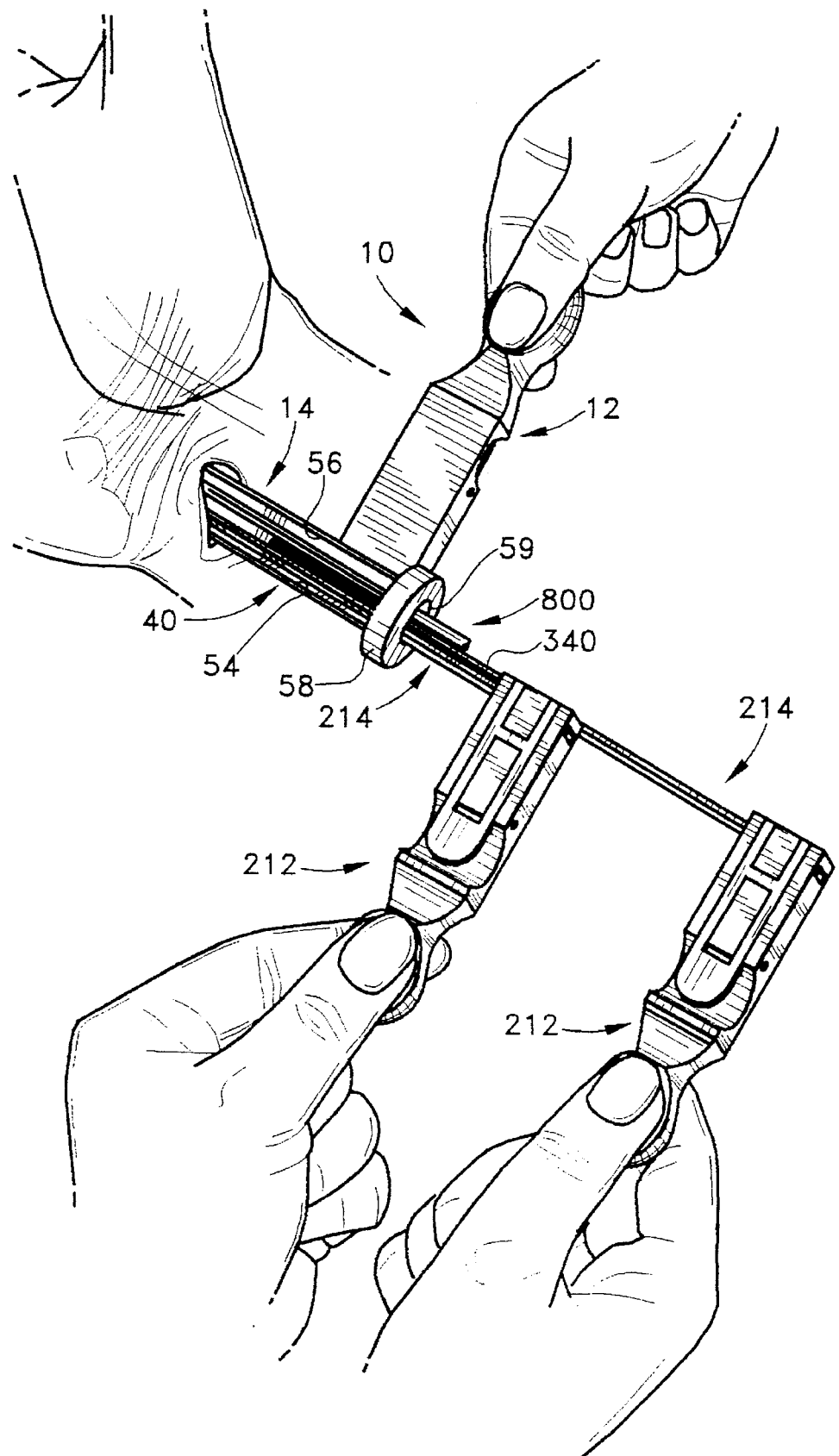
FIG. 56 is another view of a still further step during a two-handed carpal tunnel release surgical procedure using medical instrument according to the present invention.

As shown in FIG. 56, and following insertion of the endoscope 800 through channel 56 of cannula 40, one or more additional medical instruments can thence be inserted through opening 59 in tie 58 and into channel 54 of the cannula 40. As an example, a medical instrument comprised of a handle 12 having a probe or nerve hook similar to that schematically shown in FIGS. 28 or 29 and represented by reference numerals 340 and 340A, respectively, or rasps schematically represented in FIGS. 30 and 31 can be inserted through the ulnar channel 54 of cannula 40 to clear the operative field of any human debris or questionable human structures.

As schematically represented in FIG. 56, channel 54 of the dual channeled cannula 40 is sized to allow an additional medical instrument to be inserted adjacent to the probe or nerve hook 340 or 340A, or rasp already present in channel 56 of cannula 40. As will be appreciated by those skilled in the art, the additional surgical instrument 214 inserted into channel 56 of cannula 40 can take the shape of any of those cutting blades schematically illustrated in FIGS. 32 through 37. A blade having the appropriate triangular, slotted or retrograde cutting instrumentality extending upwardly from a top surface of the instrument is used to cut the ligament from distal to proximal, from proximal to distal, or within an intermediate position and cutting from the center of the ligament to the most distal and proximal extent.

During the surgical procedure, human structures may interfere with the cutting of the transverse carpal ligament. Accordingly, the probe or nerve hook 340 or 340A, which remains disposed in channel 54 of cannula 40, can be simultaneously used to slightly move, out of the path of the blade, the human structures which are not to be cut. In this regard, the surgeon S is advantageously allowed to use a two-handed technique, with one hand being used to manipulate the probe/nerve hook while the other hand is used to manipulate the cutting blade with the assistant A holding the endoscope 800.

The surgeon S may well use their dominant hand to cut the transverse carpal ligament while the surgeon's non-dominant hand manipulates the probe or nerve hook to hold the digital nerve, tendon, or median nerve out of the way of the blade. Either the handle of the blade or the handle of the probe or nerve hook should be most proximal to the patient P depending upon the length of the probe 340, 340A being used at a particular stage during the carpal tunnel release surgical procedure. Notably, the blade and probe/nerve hook are each specifically designed to allow them both to be in one of the dual channels of the cannula. Alternatively, if a cannula similar to that schematically illustrated in FIG. 14 is used, the probe can be conjointly located in channel 56 of cannula 40 in vertical relation relative to the endoscope 800.

The assistant A holds the endoscope at the location and rotation placed by the surgeon at this time only during the surgical procedure. During transection of the ligament, the blades and probes and endoscope are slowly retracted together to maintain visualization of the instruments at all time. It is also beneficial to simultaneously allow both the probe and the cutting blade to remain simultaneously disposed in the cannula such that the probe can probe the distal region of the ligament to ensure there are no residual bands requiring further cutting.

The carpal tunnel medical instruments are removed following completion of the surgical procedure. The single 1 cm incision is preferably irrigated, and the skin closed in a routine manner. A sterile compressive dressing is applied to the hand and wrist, and the tourniquet is deflated.

The present invention offers advantages that are not present with heretofore known devices. First, attaching the handle 12 at an acute angle of about 90° relative to the particular surgical instrument 14 facilitates a two-handed carpal tunnel release surgical procedure. Because the handle 12 and the particular surgical instrument 14 extending therefrom are arranged in a substantially constant plane, it allows the carpal tunnel medical instruments of the present invention to be handled by the surgeon in a traditional manner using a more natural key pinch to hold the instruments.

The double-channelled cannula 40 provides two elongated passages into the surgical region through a single portal, thus eliminating the need for a palmar incision. Avoiding a palmer incision reduces the likelihood of damage to the superficial palmar arch or common digital nerve to the third web space.

Those embodiments of the medical instrument that include a handle and surgical instrument that are releasably secured to each other offers further advantages to the present invention. The releasable interconnection between the handle and surgical instrument comprising the carpal tunnel medical instrument of the present invention means that the surgical instrument can be discarded after use, thus eliminating the concern over cross-infection between patients. The use of a releasable connection between the surgical instrument and holder also means that disposable blades can be used in combination with the medical instrument. The use of disposable blades enables sharp instruments to be available for each new operation.

A releasable connection between the handle and the surgical instrument likewise means that the handle can extend from either side of the surgical instrument without any increase in inventory costs. Ability to interchange the handle to either side of the instrument furthermore promotes a two-handed carpal tunnel release surgical procedure. When the surgeon uses both hands during the operation, the assistant A holds or manipulates the endoscope at critical points. Interchangability between blades and probes furthermore allows a number of different cutting blades including retrograde knives, pyramidal knives, triangular knives, curved banana blades, and the slotted forward cutting knife to be used depending upon the preferences of the individual surgeon. Similarly, different types of probes and different lengths of probes can be releasably attached to the holder thus enabling the surgeon to use their dominant hand for cutting with the blades while being held in a more natural fashion.

That embodiment of the invention wherein the handle and surgical instrument are embodied as a one-piece or unitary carpal tunnel medical instrument likewise offers benefits over heretofore known carpal tunnel medical devices. Because the one-piece medical structure of the present invention is disposable, it eliminates the concern over cross-infection between patients. Because it is disposable, and when the surgical instrument associated with the disposable carpal tunnel medical instrument is a cutting blade, the surgeon can rely on having a sharp new cutting edge for each new surgical procedure. The acute angular formation of about 90° between the handle portion and surgical instrument portion, whether it be a double channeled cannula, cutting knife, rasp, or probe, allows the surgeon to hold the medical instrument in a traditional approach, using a more natural key pinch hold on the medical instrument.

The above described hand holder assembly 600 allows a greater degree of flexibility and versatility in support of the patients wrists, especially in those patients who have limitations of wrist or elbow motions, or limited motion of the knuckle and finger joints as commonly experienced in older, arthritic patients. The modified endoscope 800 also described above allows for variability of rotation of the light source 806 and allows the light source to be readily removed from obstructing the surgeon's hands in the operating field.

From the foregoing, it will be observed that numerous modifications and variations can be effected without departing from the true spirit and scope of the novel concept of the present invention. It will be appreciated that the present disclosure is intended to set forth exemplifications of the invention, and are not intended to limit the invention to the specific embodiment illustrated. The disclosure is intended to cover by the appended claims all such modifications as fall within the scope of the claims.

What is claimed is:

1. A carpal tunnel medical instrument, comprising:
an elongated handle releasably attachable to and extending outwardly from either of two opposed sides of an elongated medical tool having upper and lower surfaces, and wherein, when said handle and said medical tool are releasably attached to each other, said handle extends generally normal to a longitudinal axis of said medical tool and wherein, when said handle is connected to and extends outwardly from either side of said medical tool, the top surface of said medical tool remains disposed in substantially same orientation relative to said handle thereby enhancing the versatility of the medical instrument.

2. The medical instrument according to claim 1 wherein said handle includes a grip portion configured with a downwardly slanting finger that is ergonomically configured to provide stability to the handle and to the medical tool extending therefrom.

3. The medical instrument according to claim 1 wherein the handle is configured to allow medical tools having differing configurations to be releasably associated and interchanged with the handle to add versatility to the medical instrument.

4. The medical instrument according to claim 1 wherein said medical tool is a probe.

5. The medical instrument according to claim 1 wherein said medical tool is a blade.

6. A carpal tunnel medical instrument, comprising:
an elongated handle configured to maintain a double channelled cannula in releasable association toward one end thereof, and wherein said double channelled cannula has an elongated configuration with a longitudinal axis extending generally normal to the handle when said double channelled cannula is releasably connected to said handle.

7. The medical instrument according to claim 6 wherein said double channelled cannula has a top surface with side surfaces extending therefrom.

8. The medical instrument according to claim 7 wherein the handle is configured such that the handle can be releasably associated with and extend from either side of the double channelled cannula.

9. A carpal tunnel medical instrument comprising:
an elongated handle having an ergonomically configured grip portion provided at one end thereof;
an elongated surgical instrument having a top surface and first and second generally axially aligned ends, with the first end of said instrument being releasably secured toward a second end of said handle, and wherein the top surface of the surgical instrument is orientated in a predetermined manner relative to and such that said surgical instrument extends at about a 90 degree angle from said handle; and
a manually operated locking mechanism for releasably securing the surgical instrument to the handle such that the handle can extend outwardly from either side of the surgical instrument while maintaining the predetermined orientation between the top surface of the surgical instrument and the handle.

10. The medical instrument according to claim 9 wherein said surgical instrument has at least two axially spaced notches that open to the top surface of said surgical instrument and are arranged adjacent to the first end of said surgical instrument.

11. The medical instrument according claim 10 wherein said handle has front and rear faces that are spaced apart by a predetermined distance.

12. The medical instrument according to claim 11 wherein the axial spacing between said notches in said surgical instrument is less than the spacing between said front and rear faces of said handle.

13. The medical instrument according to claim 10 wherein said locking mechanism comprises a spring biased lever carried by said handle, with a first end of said lever being adapted to interlock with the axially spaced notches on the surgical instrument thereby releasably securing the surgical instrument to the handle.

14. The medical instrument according to claim 13 wherein said spring biased lever of the locking mechanism is pivotally connected between opposite ends to said handle, and wherein a second end of said lever is disposed for manual engagement to rock the lever between engaged and released positions.

15. The medical instrument according to claim 9 wherein said handle is provided with a bore for endwise accommodating the surgical instrument, and wherein a closed margin of said bore provides stability to the surgical instrument received therein.

16. The medical instrument according to claim 15 wherein the bore in said handle is configured to correspond to the cross-sectional configuration at the first end of said surgical instrument.

17. The medical instrument according to claim 9 wherein said surgical instrument is a probe having an instrumentality extending upwardly from the top surface of the instrument.

18. The medical instrument according to claim 9 wherein said surgical instrument is a blade having at least one cutting instrumentality extending upwardly from the top surface of the instrument.

19. The medical instrument according to claim 9 wherein said surgical instrument is a double channelled cannula having adjacent channels that each open to a top side of the surgical instrument.

20. The medical instrument according to claim 19 wherein both channels of the double channelled cannula are closed at the distal end thereof.

21. The medical instrument according to claim 19 wherein said surgical instrument is a double channelled cannula including a tie that joins the double channels of the cannula to each other at a first end of the instrument and is disposed to a side of the handle opposite from that side from which the surgical instrument extends.

22. The medical instrument according to claim 19 wherein said double channelled cannula is formed from stainless steel.

23. The medical instrument according to claim 9 wherein said surgical instrument is formed from a polycarbonate material and is disposable following completion of a surgical procedure.

24. A carpal tunnel medical instrument, comprising:
an elongated surgical instrument having axially aligned first and second ends with a top surface and a pair of generally parallel side surfaces; and
an elongated handle for stabilizing the surgical instrument releasably connected at a first end to the handle and wherein said handle extends generally normal to said surgical instrument, the releasable connection between the housing and said surgical instrument permitting said handle to be operably connected to and yet extend outwardly from either side of the medical instrument while maintaining a consistent relationship between the top surface of the surgical instrument and the handle.

25. The medical instrument according to claim 24 further including a locking mechanism carried by said handle between front and rear faces thereof for releasably securing the surgical instrument against displacement relative to said handle.

26. The medical instrument according to claim 24 wherein said surgical instrument is a probe having an instrumentality extending upwardly from the second end of said surgical instrument.

27. The medical instrument according to claim 24 wherein each probe has a generally rectangular cross sectional configuration at least at the first end thereof.

28. The medical instrument according to claim 24 wherein said surgical instrument is a blade having at least one cutting instrumentality upwardly extending from the top surface and arranged toward a second end of said surgical instrument.

29. The medical instrument according to claim 28 wherein each blade has a generally rectangular cross sectional configuration at least at the first end thereof.

30. The medical instrument according to claim 24 wherein said surgical instrument is a double channelled cannula, with both channels of the cannula opening to the top surface of the surgical instrument.

31. A one-piece carpal tunnel medical instrument, comprising:

an elongated surgical instrument portion that is configured as either a double channeled cannula, a cutting blade, a probe, or a rasp, said surgical instrument having a generally planar top surface and a handle portion extending at an acute angle from the surgical instrument portion and in a plane substantially parallel to the planar top surface of the surgical instrument portion.

32. The medical instrument according to claim 31 wherein said handle portion includes an ergonomically configured grip at the distal end to promote stabilization of the medical instrument.

33. The medical instrument according to claim 31 wherein said surgical instrument portion is configured as a probe having an instrumentality disposed at the distal end thereof and extending upwardly from the top surface thereof.

34. The medical instrument according to claim 31 wherein said surgical instrument portion is configured as a blade having at least one cutting instrumentality disposed at the distal end thereof and extending upwardly from a top surface thereof.

35. The medical instrument according to claim 31 wherein said surgical instrument portion is configured as a double channelled cannula defining two adjacent channels that extend substantially the length of said surgical instrument portion, with each channel opening to the top surface of the surgical instrument portion.

36. The medical instrument according to claim 35 wherein the distal end of each channel of the double channelled cannula is closed.

37. The medical instrument according to claim 31 wherein the surgical instrument portion and the handle portion are integrally formed from a polycarbonate material.

38. A carpal tunnel release medical kit, comprising:

a plurality of individual medical instruments used in combination relative to each other during a carpal tunnel release surgical procedure, said medical instruments including a dual channeled cannula having first and second elongated and adjacent channels that are separated from each other and terminate at a substantially common length in a blunt end, with each channel being sized to allow an endoscope to pass endwise therethrough, an elongated cutting blade including a top surface extending substantially the length of said blade and having a cutting instrumentality extending upwardly from the top surface at one end of the blade and with a handle extending at an acute angle away from a side of and at the opposite end of said blade to stabilize the blade during the surgical procedure, and an elongated probe including a top surface extending substantially the length of the probe and having an instrumentality extending upwardly from the top surface at one end of the probe and a handle extending outwardly at an acute angle away from the side of and at an opposite end of the probe to stabilize the probe during the surgical procedure, and wherein the handle on the blade extends in a first direction while the handle on the probe similarly extends in the same direction but can be used in the opposite direction to promote two-handed manipulation of the surgical instruments during the surgical procedure.

* * * * *